United States Patent
Del Soldato et al.

(10) Patent No.: US 6,794,372 B2
(45) Date of Patent: Sep. 21, 2004

(54) NITRATE SALTS OF ANTIMICROBIAL AGENTS

(75) Inventors: Piero Del Soldato, Monza (IT); Francesca Benedini, Milan (IT); Patrizia Antognazza, Milan (IT)

(73) Assignee: Nicox S.A., Sophia Antipolis (FR)

(*) Notice: Subject to any disclaimer, the term of this patent is extended or adjusted under 35 U.S.C. 154(b) by 0 days.

(21) Appl. No.: 10/181,424

(22) PCT Filed: Jan. 16, 2001

(86) PCT No.: PCT/EP01/00430

§ 371 (c)(1), (2), (4) Date: Jul. 24, 2002

(87) PCT Pub. No.: WO01/54691

PCT Pub. Date: Aug. 2, 2001

(65) Prior Publication Data

US 2003/0105066 A1 Jun. 5, 2003

(30) Foreign Application Priority Data

Jan. 26, 2000 (IT) .................................. MI2000A0092

(51) Int. Cl.$^7$ .................. A61K 31/365; C07D 221/02; C07D 471/02

(52) U.S. Cl. .......................... 514/81; 546/112; 546/113

(58) Field of Search .................................. 546/112, 113; 514/81

(56) References Cited

U.S. PATENT DOCUMENTS

| | | | | |
|---|---|---|---|---|
| 6,410,791 B1 | * | 6/2002 | Soldato | 564/361 |
| 6,503,929 B1 | * | 1/2003 | Del Soldato | 514/338 |
| 6,573,252 B1 | * | 6/2003 | Del Soldato | 514/108 |
| 6,645,965 B1 | * | 11/2003 | Del Soldato | 514/248 |

OTHER PUBLICATIONS

Remington's Pharmaceuticals Science, 15a Ed., 1975.
Merck index, 12a Ed., 1996.
Manual of Clinical Microbiology, 5th Ed., 1991, American Society for Microbiology, Sahm et al., "Antibacterial susceptibility tests: dilution methods".
"Methods for Dilution Antimicrobial Susceptibility Tests for Bacteria that Grow Aerobically", Approved Standard M7–A2, NCCLS, vol. 10, No. 8, pp. i–iii.

* cited by examiner

Primary Examiner—Elli Peselev
(74) Attorney, Agent, or Firm—Arent Fox

(57) ABSTRACT

Nitrate salts of antimicrobial agents for the preparation of antimicrobial medicaments, specifically antiviral, antifungal and antibacterial medicaments.

20 Claims, No Drawings

NITRATE SALTS OF ANTIMICROBIAL AGENTS

CROSS-REFERENCE TO RELATED APPLICATION

This application is a National Stage entry of International Application No. PCT/EP01/00430, filed Jan. 16, 2001, the entire specification, claims and drawings of which are incorporated herewith by reference.

The present invention relates to compounds, or their pharmaceutical compositions, for systemic use and non, to be used in the antimicrobial therapy.

It is known that the wide use of antimicrobial agents in the infection treatment has caused the development of strains resistant to these drugs, for example the case of antiviral, antifungal and antibacterial agents can be mentioned.

This resistance generally arises when microorganisms develop growth and reproduction mechanisms on which the antimicrobial therapy is ineffective, or when the microorganisms produce enzymes which neutralize the drug. The resistant microbial strain is then able to multiply, causing the illness prolongation and worsening, with possible diffusion of the infection in the communities. This fact, as known, can determine notable consequences at a social-economic and sanitary level.

A method to solve this problem is to increase the dosage of the antimicrobial drugs. In this way there is the drawback of an increased incidence of side effects both local and systemic. Besides, cases of microbial superinfection deriving from the antimicrobial agent itself due to the inbalance between pathogen and non pathogen microbial flora often occur. It is well known that antimicrobial agents must act on the pathogen agents which are responsible of the unhealthy process and leave unaltered the non pathogen microbes useful for the organism.

A widely followed approach for solving the problem of the microbial resistance, and/or of the diffusion of pharmaco-resistant strains, has been to introduce in therapy new molecules to be used as antimicrobial agents. The results so far obtained are not satisfactory.

The need was therefore felt to have available drugs able not only to be active on the microorganism but also to prevent and/or reduce the microbial resistance and therefore to allow a complete and effective antimicrobial therapy, said drugs being effective at the conventional minimum dosages to avoid the side toxic effects. Among the latter skin rash and the effects on the stomach, liver and kidney can for example be mentioned.

It has been surprisingly and unexpectedly found by the Applicant that it is possible to solve the above technical problem by using compounds which have shown to be able to effectively interact with microbes and to prevent or reduce the microbial resistance.

An object of the present invention is the use of nitrate salts of antimicrobial agents, or their pharmaceutical compositions, for the preparation of medicaments usable in the treatment of infectious diseases. Preferably the invention relates to the use of nitrate salts of antiviral, antifungal and antibacterial agents, or their pharmaceutical compositions; the antimicrobial agents usable for preparing the nitrate salts of the present invention must satisfy the following test: in the culture of specific pathogen microbes responsible for the single pathologies, the antimicrobial agent is inoculated at a concentration such as to result effective as antimicrobial agent and such as not to produce cytotoxicity in mammalian cells.

See for example the test of the dilution in vitro on medium reported in the Examples for the antibacterial agents.

More specifically the present invention relates to the use of nitrate salts of compounds, or their pharmaceutical compositions, for preparing medicaments usable in the treatment of infectious diseases as antimicrobial agents, said compounds preferably being selected from the following classes:

class I)

(I)

wherein:
$R_1$=H, Cl or dimethylamino,
$R_2$=H, OH, or free valence,
$R_3$=H, $CH_3$, when $R_2$ is free valence with the doublet of the C—$R_3$ bond it forms a double bond and $R_3$ is methylene,
$R_4$=H, OH,
$R_5$=H, $CH_2OH$, or one of the following substituents:

(IA)

(IB)

(IC)

(ID)

class II)

(II)

wherein:
X and Y, different the one from the other, are C or N,
$R_6$=ciclopropyl, $C_2H_5$, 4-fluorophenyl, 2,4-difluorophenyl, 2-fluoroethyl,
$R_7$=H, amino, $CH_3$, $R_8$=H or F, when Y=N, $R_8$ is free valence and it is the free doublet on the nitrogen atom, $R_9$=H, $CH_3$ or one of the following substituents:

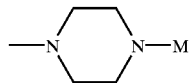
(IIA)

wherein M=H, $CH_3$, $C_2H_5$, OH,

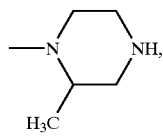
(IIB)

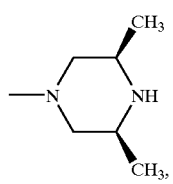
(IIC)

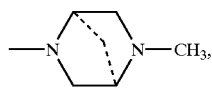
(IID)

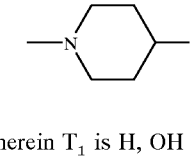
(IIE)

wherein $T_1$ is H, OH

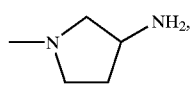
(IIF)

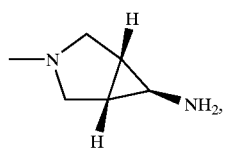
(IIG)

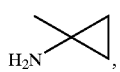
(IIH)

$R_8$ and $R_9$ taken together form the bivalent radical having formula: —O—$CH_2$—O— (IIP), $R_{10}$=H, Cl, F, when X=N, $R_{10}$ is free valence and it is the free doublet on the nitrogen atom, $R_6$ and $R_{10}$ taken together form the following bivalent radicals:

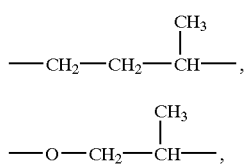
(IIM)

(IIN)

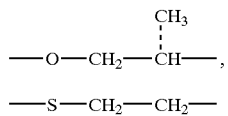
(IIO)

(IIQ)

when X in the formula (II)=N, $R_{10}$ is free valence and it forms a double bond with the carbon atom adjacent to the nitrogen;

class IIIa):

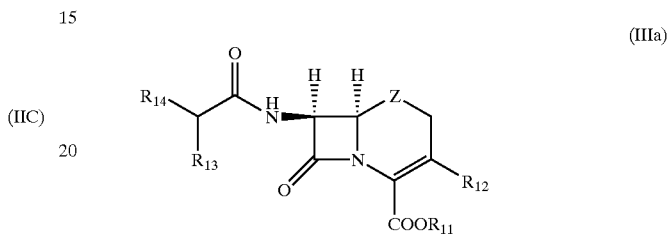
(IIIa)

wherein:

Z=S, C, $R_{11}$=H, pivaloyloxymethylene of formula (IIIaF) wherein $T_2$ is the tert-butyl group, $R_{12}$=Cl, $CH_3$, acetyloxymethylene of formula (IIIaF) wherein $T_2$ is $CH_3$, 2-propenyl or one of the following substituents:

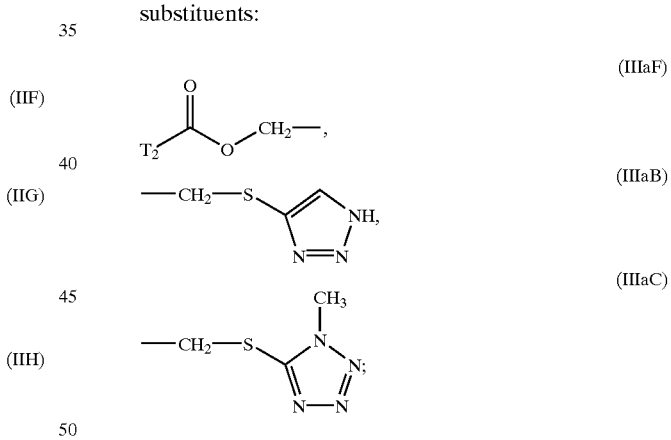
(IIIaF)

(IIIaB)

(IIIaC)

$R_{13}$=amino, OH, or the substituent (IIIaD):

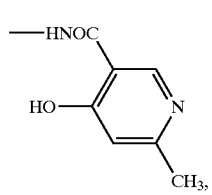
(IIIaD)

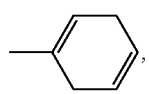
(IIIaE)

$R_{14}$ is phenyl, 4-hydroxyphenyl, or the radical (IIIaE);

class IIIb)

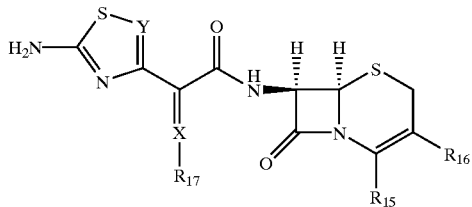
(IIIb)

wherein:

X=CH, N.
Y=C, N,
R$_{15}$=COOH, COO$^-$, (CH$_3$)$_3$CCOOCH$_2$OCO— or (CH$_3$)$_2$CHOCOOCH(CH$_3$)OCO—,
R$_{16}$=H, CH$_3$, C$_2$H$_5$, —CH=CH$_2$, NH$_2$COOCH$_2$—, CH$_3$COOCH$_2$—, or one of the following substituents:

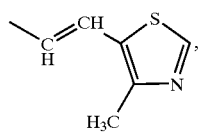
(IIIbA)

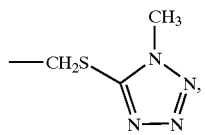
(IIIbC)

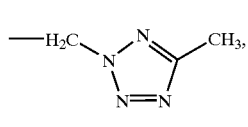
(IIIbD)

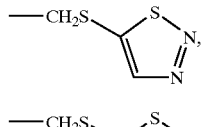
(IIIbE)

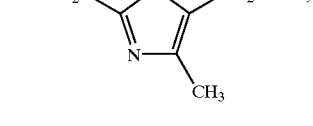
(IIIbF)

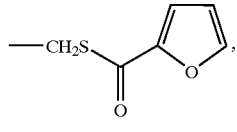
(IIIbG)

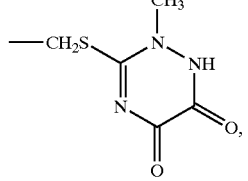
(IIIbH)

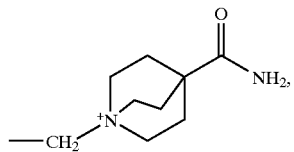
(IIIbL)

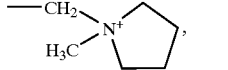
(IIIbM)

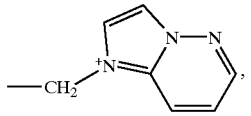
(IIIbN)

when R$_{15}$ is carboxylated anion R$_{16}$ is a radical selected from the following: (IIIbL), (IIIbM) or (IIIbN)

R$_{17}$=OH, OCH$_3$, C$_2$H$_5$, —OCH$_2$COOH, —CH$_2$COOH;

class IIIc)

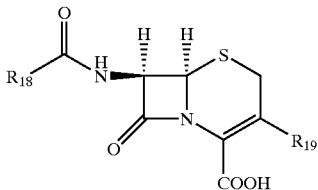
(IIIc)

wherein:

R$_{18}$ is one of the following substituents:

(IIIcA)

(IIIcB)

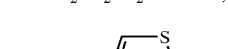
(IIIcD)

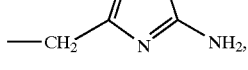
(IIIcE)

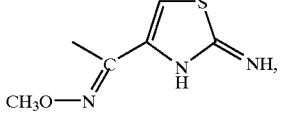
(IIIcF)

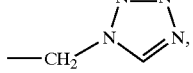
(IIIcG)

R$_{19}$=H, CH$_3$COOCH$_2$—, or one of the following groups:

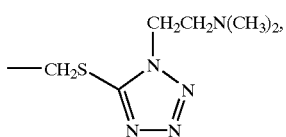
(IIIcH)

class IVa:
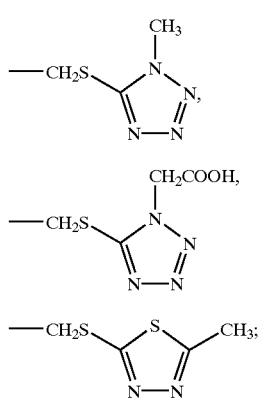
wherein:
$R_{20}$ is one of the following substituents:
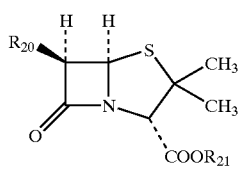 (IVaA)
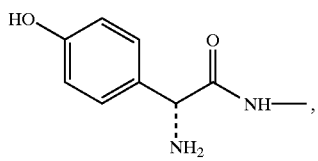 (IVaB)
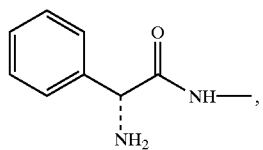 (IVaC)
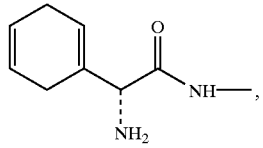 (IVaD)
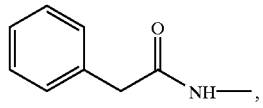 (IVaE)
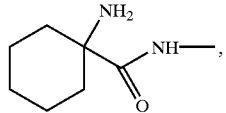 (IVaF)
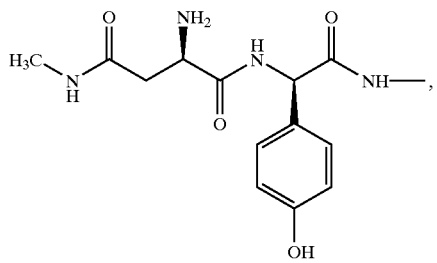 (IVaG)
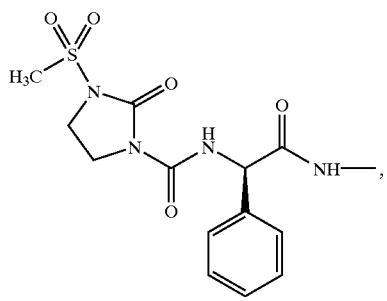 (IVaH)
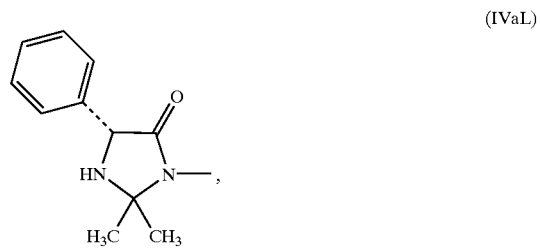 (IVaL)
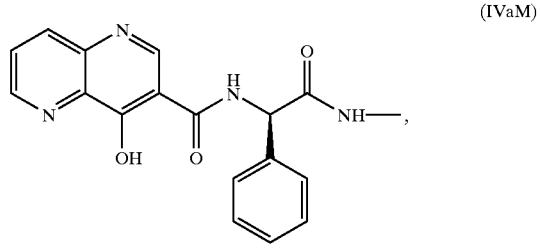 (IVaM)
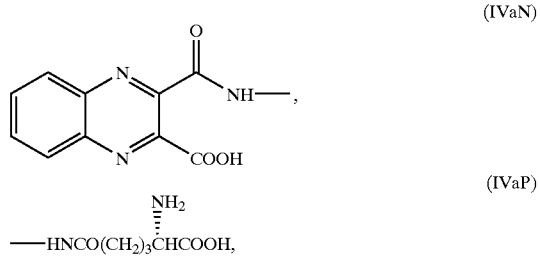 (IVaN)
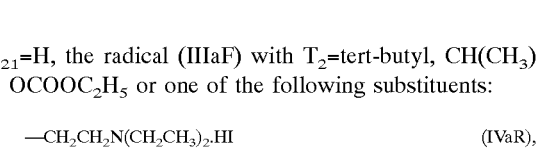 (IVaP)
$R_{21}$=H, the radical (IIIaF) with $T_2$=tert-butyl, CH(CH$_3$)OCOOC$_2$H$_5$ or one of the following substituents:
—CH$_2$CH$_2$N(CH$_2$CH$_3$)$_2$.HI (IVaR),
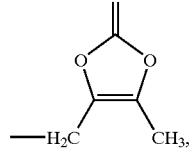 (IVaS)

-continued
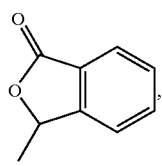
(IVaT)
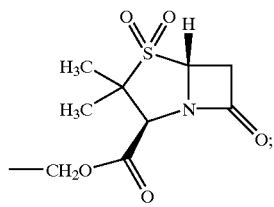
class IVb)
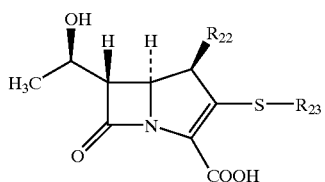
wherein:
R₂₂=H, CH₃,
R₂₃ is selected from the following groups:
—CH₂CH₂NHCH=NH    (IVbD),
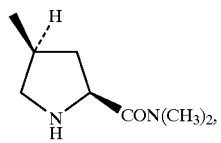    (IVbA)
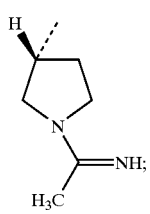    (IVbC)
class IVc)
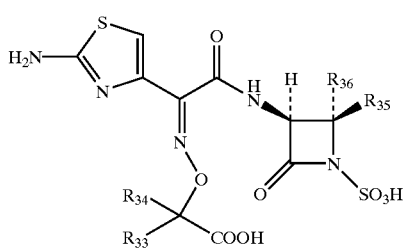    (IVc)
wherein:
R₃₃, R₃₄, R₃₆, equal to or different from each other, are H, CH₃;
R₃₅=H, —CH₂OCONH₂,
class V)
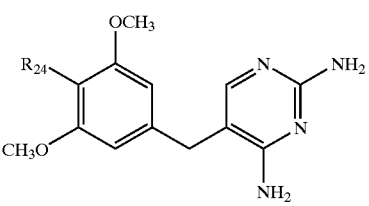    (V)
wherein
R₂₄=H, Br, OCH₃, CH₃OCH₂CH₂O—;
class VI)
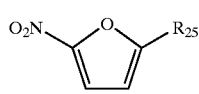    (VI)
wherein:
R₂₅ is one of the following substituents:
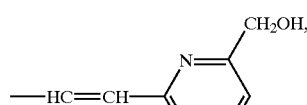    (VIA)
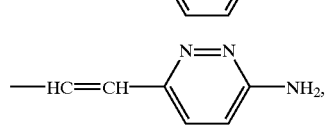    (VIB)
    (VIC)
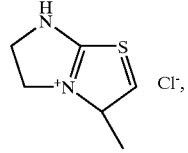
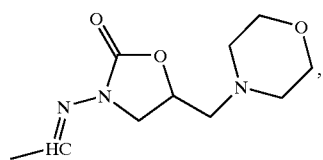    (VID)
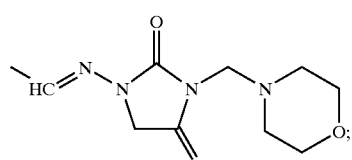    (VIE)
class VII)
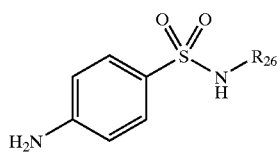    (VII)
wherein $R_{26}$=H, or one of the following substituents: benzoyl, acetyl, 3-methyl-2-butenoyl, carbamoyl, aminothioxo $NH_2C(S)$— 2-pyridinyl, pyrazinyl, 2-pyrimidinyl, 2-thiazolyl, salicyl-4-yl, 6-chloro-pyridazine-3-yl, 1-ethyl-1,2-dihydro-2-oxo-pyrimidin-4-yl, 5,6-dimethoxy-pyrimidin-4-yl, 2,6-dimethoxy-Pyrimidin-4-yl, 4-methyl-pyrimidin-2-yl, 5-methoxy-pyrimidin-2-yl, 4,6-dimethyl-pyrimidin-2-yl, 6-methoxy-2-methyl-pyrimidin-4-yl, 5-methyl-pyrimidin-2-yl, 2,6-dimethyl pyrimidin-4-yl, 3-methoxy-pyrazine-2-yl, 6-methoxy-pyridazin-3-yl, 4,6-diethyl-1,3,5-triazin-2-yl, 5-ethyl-1,3,4-thiadiazol-2-yl, 5-methyl-1,3,4-thiadiazol-2-yl, 4-methoxy-1,2,5-thiadiazol-3-yl, 4-methyl-thiazol-2-yl, 3-methyl-isothiazol-5-yl, 4,5-dimethyl-oxazol-2-yl, 3,4-dimethyl-isooxazol-5-yl, 4,5-dimethyl-2-oxazolylaminoiminomethyl, 5-methyl-isooxazol-3-yl, 1-phenyl-1H-pyrazol-5-yl, 4-methylamino sulphonylphenyl, 4-amino-sulphonylphenyl, 3,4-dimethylbenzoyl, 4-isopropoxy benzoyl;

class VIII)

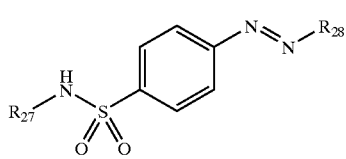

wherein:

$R_{27}$=H, 4,6-dimethyl-pyrimidin-2-yl;
$R_{28}$=2,4-diamino-6-carboxyphenyl, 2,4-diaminophenyl, 3-car-boxy-4-hydroxyphenyl;

class IX)

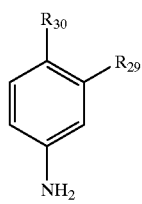
(IX)

wherein:

$R_{29}$=H, OH,
$R_{30}$=COOH, phenoxycarbonyl, 4-(amino)phenylsulphinyl, hydra-zinecarbonyl;

class X)

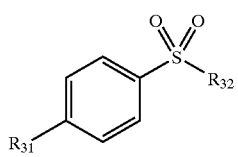
(X)

wherein:

$R_{31}$=amino, $NH_2$—$CH_2$—, benzylamino,
$R_{32}$=amino, 4-(hydroxyethylamino)phenyl, —N═C$(NH_2)_2$, 4-(amino)phenyl, 4-(aminomethyl) phenyl, 4-(carboxymethyl amino)phenyl, 4-(carboxypropionyl amino)phenyl, 2-amino-thiazol-5-yl;

class XI)

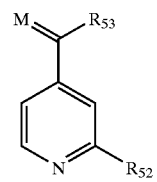
(XI)

wherein:

M=O, S,
$R_{52}$=H, $C_2H_5$, $C_3H_7$,
$R_{53}$=amino, —$NHNH_2$, or one of the following substituents:

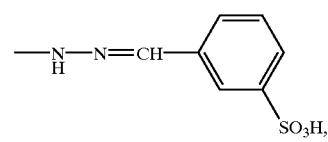
(XIA)

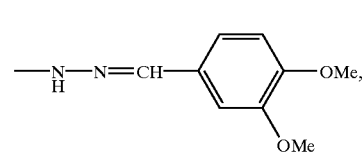
(XIB)

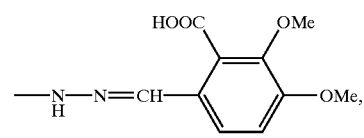
(XIC)

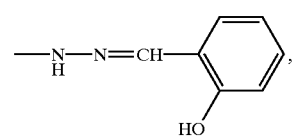
(XID)

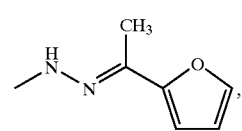
(XIE)

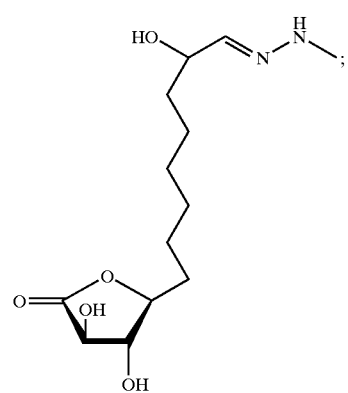
(XIF)

class XII)

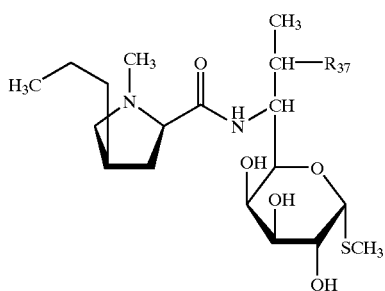
(XII)

wherein:
R_{37}=Cl, OH;

class XIIIa)

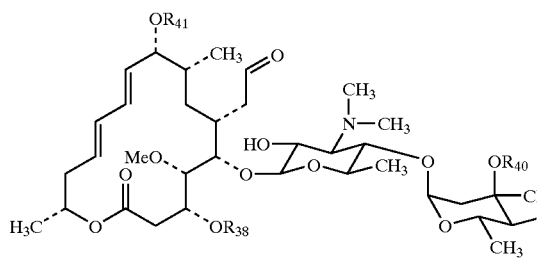
(XIIIa)

wherein:
R_{38}=H, acetyl, $COC_2H_5$ (propionyl),
R_{39}=H, propionyl, $COC_3H_7$ (butyryl), $COCH_2CH(CH_3)_2$ (isovaleryl),
R_{40}=H, propionyl,
R_{41}=H, or:

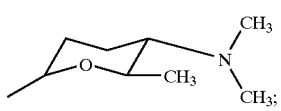
(XIIIaB)

class XIIIb)

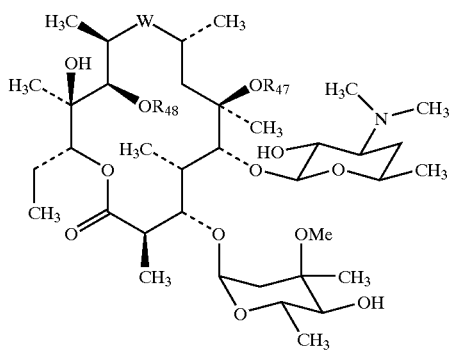
(XIIIb)

wherein:
R_{47}=H, $CH_3$,
W=CO (carbonyl), —$N(CH_3)CH_2$—,

R_{48}=H, or R_{48} together with W forms the bivalent radical:

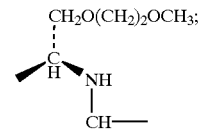
(XIIIbA)

class XIVa)

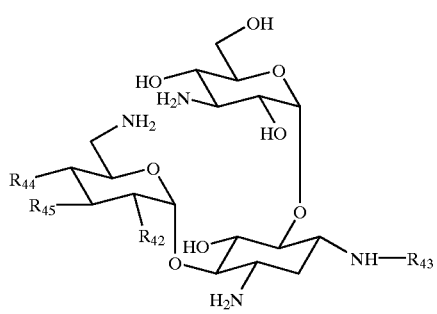
(XIVa)

wherein:
R_{42}=OH, amino,
R_{43}=H, (R)-4-amino-2-hydroxybutyryl, (S)-4-amino-2-hydroxybutyryl,
R_{44}=H, OH,
R_{45}=H, OH;

class XIVb)

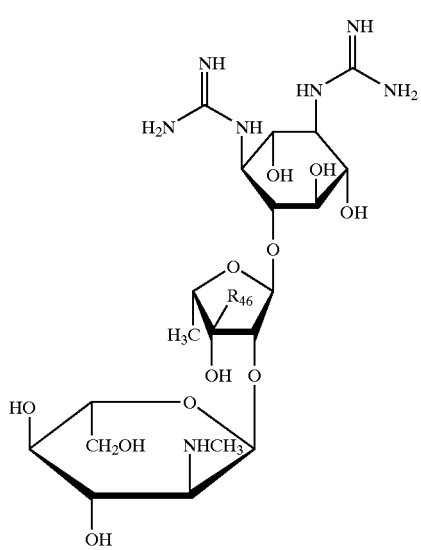
(XIVb)

wherein:
R_{46}=—$CH_2OH$; —CHO

Class XIVc)

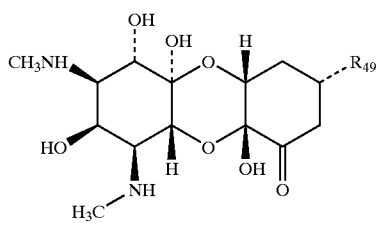
(XIVc)

wherein:

$R_{49}=CH_3, C_4H_9$;

class XIVd)

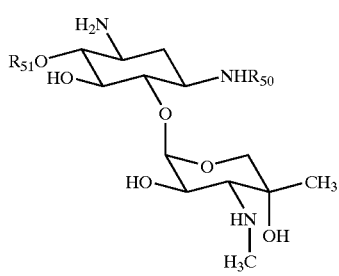
(XIVd)

wherein:

$R_{50}=H, C_2H_5$,
$R_{51}=$3-amino-6-(aminomethyl)-3,4-dihydro-2H-pyran-2-yl:

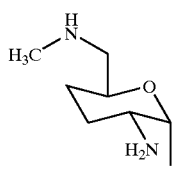
(XIVdA)

Class XIVe)

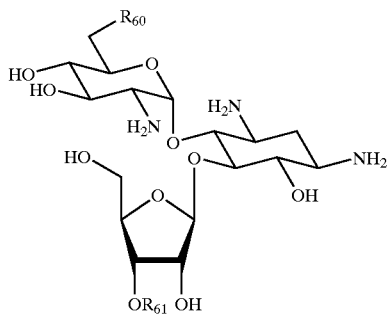
(XIVe)

wherein:

$R_{60}=OH$, amino, $R_{61}=H$ or one of the following substituents:

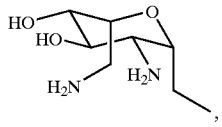
(XIVeA)

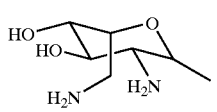
(XIVeB)

Class XV)

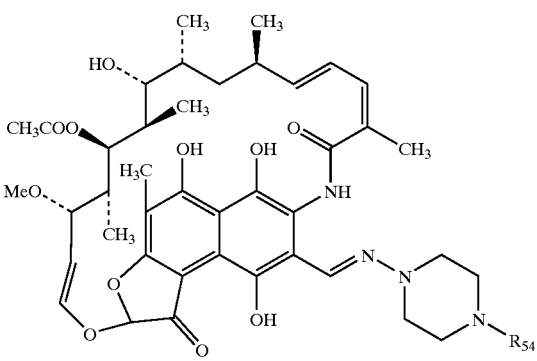

wherein $R_{54}=CH_3$, cyclopentyl;

Class XVIa)

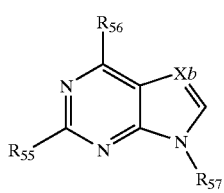
(XVIa)

wherein:

$X_b=N, C$,
$R_{55}=H$, amino,
$R_{56}=H, OH$, amino,
$R_{57}$ é β-D-ribofuranosyl or 4-acetoxy-3-(acetoxymethyl) 1-bu-tyl;

Class XVIb)

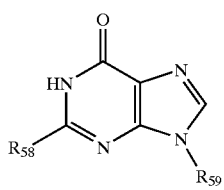
(XVIb)

wherein:

$R_{58}=H$, amino,
$R_{59}=CH_2OCH_2CH_2OH$, $CH_2OCH(CH_2OH)CH_2OH$, $CH_2OCH_2CH_2OCOCH(NH_2)CH(CH_3)_2$, β-D-(2,3-dideoxy)ribofuranosyl;

Class XVII): the following compounds:

O-2-amino-2-deoxy-α-D-glucopyranosyl-(1→4)-O-[3-deoxy-3-(methylamino)-α-D-xylopyranosyl-(1→6)]-2-deoxy-D-streptamine (Gentamycin A), 1-(2-hydroxyethyl)-2-methyl-5-nitroimidazol (Metronidazole), (S)-2-amino-5-[(aminoiminomethyl)amino]pentanoic acid (Arginine), (+)-2,2'-(ethylendiimino)di-1-butanol (Ethambutol), 1-aminoadamantane (Amantadine), 2',3'-dideoxy-cytidine (zalcitabine), Pyrazinamide, Morfazinamide, Acetylsulfamethoxypyrazine, Clofazimine, Cycloserine, Streptonicizid, Deoxydihydrostreptomycin, Mikamycin, Rosaramicin, Carbomycin, Alexidine, Ambazone, Cloxiquin, Negamycin, Nitroxoline, Porfiromycin, Taurolidine, Tibezonium iodide, Apramycin, Teicoplanin, Vancomycin, Thiabendazole, Mebendazole, Albendazole, Acranil, Anisomycin, Dimetridazole, Diminazene, Aceturate, Eflornithine, Halofuginone, Homidium, Hydroxystilbamidine, Imidocarb, Ipronidazole, Lauroguadine, Nimorazole, Oxophenarsine, Pentamidine, Phenamidine, Propamidine, Puromycin, Pyrimethamine, Quinacrine, Quinapyramine, Quintine, Secnidazole, Stilbamidine, Tinidazole.

In class I:
when $R_1$=H, $R_2$=OH, $R_3$=CH$_3$, $R_4$=H, $R_5$=(IA), the compound is known as Apicycline, when $R_1$=Cl, $R_2$=OH, $R_3$=CH$_3$, $R_4$=H, $R_5$=H, the compound is known as Chlortetracycline, when $R_1$=Cl, $R_2$=OH, $R_3$=CH$_3$, $R_4$=H, $R_5$=CH$_2$OH, the compound is known as Clomocycline, when $R_1$=Cl, $R_2$=OH, $R_3$=H, $R_4$=H, $R_5$=H, the compound is known as Demeclocycline, when $R_1$=H, $R_2$=H, $R_3$=CH$_3$, $R_4$=OH, $R_5$=H, the compound is known as Doxycycline, when $R_1$=H, $R_2$=OH, $R_3$=CH$_3$, $R_4$=H, $R_5$=(IB), the compound is known as Guamecycline, when $R_1$=H, $R_2$=OH, $R_3$=CH$_3$, $R_4$=H, $R_5$=(ID), the compound is known as Lymecycline, when $R_1$=Cl, $R_2$=free valence and with the doublet of the C—$R_3$ bond it forms a double bond, and $R_3$ is methylene, $R_4$=OH, $R_5$=H, the compound is known as Meclocycline, when $R_1$=H, $R_2$=free valence and with the doublet of the C—$R_3$ bond it forms a double bond, and $R_3$ is methylene, $R_4$=OH, $R_5$=H, the compound is known as Methacycline, when $R_1$=dimethylamino, $R_2$=H, $R_3$=H, $R_4$=H, $R_5$=H, the compound is known as Minocycline, when $R_1$=H, $R_2$=OH, $R_3$=H, $R_4$=OH, $R_5$=H, the compound is known as Oxytetracycline, when $R_1$=H, $R_2$=OH, $R_3$=CH$_3$, $R_4$=H, $R_5$=(IC), the compound is known as Pipacycline, when $R_1$=H, $R_2$=OH, $R_3$=CH$_3$, $R_4$=H, $R_5$=H, the compound is known as Tetracycline;

when $R_1$=H, $R_2$=H, $R_3$=H, $R_4$=H, $R_5$=H, the compound is known as Sancycline.

In class II:
when $R_6$=cyclopropyl, $R_7$=H, $R_8$=F, $R_9$=(IIA) with M=H, $R_{10}$=H, X=Y=C, the compound is known as Ciprofloxacin, when $R_6$=cyclopropyl, $R_7$=H, $R_8$=F, $R_9$=(IIF), $R_{10}$=Cl, X=Y=C, the compound is known as Clinaloxacin, when $R_6$=4-fluorophenyl, $R_7$=H, $R_8$=F, $R_9$=(IID), $R_{10}$=H, X=Y=C, the compound is known as Difloxacin, when $R_6$=C$_2$H$_5$, $R_7$=H, $R_8$=F, $R_9$=(IIA) with M=H, $R_{10}$=free valence, X=N, Y=C, the compound is known as Enoxacin, when $R_6$=cyclopropyl, $R_7$=H, $R_8$=F, $R_9$=(IIA) with M=C$_2$H$_5$, $R_{10}$=H, X=Y=C, the compound is known as Enrofloxacin, when $R_6$=fluoroethyl, $R_7$=H, $R_8$=F, $R_9$=(IIA) with M=CH$_3$, $R_{10}$=F, X=Y=C, the compound is known as Fleroxacin, when $R_6$ with $R_{10}$ forms the bivalent radical (IIM), $R_7$=H, $R_8$=F, $R_9$=H, X=Y=C, the compound is known as Flumequine, when $R_6$=cyclopropyl, $R_7$=CH$_3$, $R_8$=F, $R_9$=(IIB), $R_{10}$=H, X=Y=C, the compound is known as Grepafloxacin, when $R_6$=ethyl, $R_7$=H, $R_8$=F, $R_9$=(IIB), $R_{10}$=F, X=Y=C, the compound is known as Lomefloxacin, when $R_6$ with $R_{10}$ forms the bivalent radical (IIM), $R_7$=H, $R_8$=F, $R_9$=(IIE) with $T_1$=OH, X=Y=C, the compound is known as Nadifloxacin, when $R_6$=C$_2$H$_5$, $R_7$=H, $R_8$=H, $R_9$=CH$_3$, $R_{10}$=free valence, X=N, Y=C, the compound is known as Nalidixic acid, when $R_6$=C$_2$H$_5$, $R_7$=H, $R_8$=F, $R_9$=(IIA) with M=H, $R_{10}$=H, X=Y=C, the compound is known as Norfloxacin, when $R_6$ with $R_{10}$ forms the bivalent radical (IIN), $R_7$=H, $R_8$=F, $R_9$=(IIA) with M=CH$_3$, X=Y=C, the compound is known as Ofloxacin, when $R_6$=C$_2$H$_5$, $R_7$=H, $R_8$ and $R_9$ form the bivalent radical (IIP), $R_{10}$=H, X=Y=C, the compound is known as Oxolinic acid, when $R_6$ with $R_{10}$ forms the bivalent radical (IIO), $R_7$=H, $R_8$=F, $R_9$=(IIH), X=Y=C, the compound is known as Pazufloxacin, when $R_6$=ethyl, $R_7$=H, F, $R_9$=(IIA) with M=CH$_3$, $R_{10}$=H, X=Y=C, the compound is known as Pefloxacin, when $R_6$=C$_2$H$_5$, $R_7$=H, $R_8$=free valence, $R_9$=(IIA) with M=H, $R_{10}$=free valence, X=Y=N, the compound is known as Pipeimidic acid, when $R_6$=C$_2$H$_5$, $R_7$=H, $R_8$=free valence, $R_9$=(IIE) with $T_1$=H, $R_{10}$=fre valence, X=Y=N, the compound is known as Piromidic acid, when $R_6$ with $R_{10}$ forms the bivalent radical (IIQ), $R_7$=H, $R_8$=F, $R_9$=(IIA) with M=CH$_3$, X=Y=C, the compound is known as Rufloxacin, when $R_6$=cyclopropyl, $R_7$=amino, $R_8$=F, $R_9$=(IIC), $R_{10}$=F, X=Y=C, the compound is known as Sparfloxacin, when $R_6$=2,4-difluorophenyl, $R_7$=H, $R_8$=F, $R_9$=(IIF), $R_{10}$=free valence, X=N, Y=C, the compound is known as Tosufloxacin, when $R_6$=2,4-difluorophenyl, $R_7$=H, $R_8$=F, $R_9$=(IIG), $R_{10}$=free valence, X=N, Y=C, the compound is known as Trovafloxacin, when $R_6$=cyclopropyl, $R_7$=H, $R_8$=F, $R_9$=(IID), $R_{10}$=H, X=Y=C, the compound is known as Danofloxacin, when $R_6$=4-fluorophenyl, $R_7$=H, $R_8$=F, $R_9$=(IIA) with M=H, $R_{10}$=H, X=Y=C, the compound is known as Sarafloxacin.

In class IIIa:
when $R_{11}$=H, $R_{12}$=Cl, $R_{13}$=amino, $R_{14}$=phenyl, Z=S, the compound is known as Cefaclor, when $R_{11}$=H, $R_{12}$=CH$_3$, $R_{13}$=amino, $R_{14}$=4-hydroxyphenyl, Z=S, the compound is known as Cefafroxil, when $R_{11}$=H, $R_{12}$=(IIIaB), $R_{13}$=amino, $R_{14}$=4-hydroxyphenyl, Z=S, the compound is known as Cefatrizine, when $R_{11}$=H, $R_{12}$=(IIIaC), $R_{13}$=(IIIaD), $R_{14}$=4-hydroxyphenyl, Z=S, the compound is known as Cefpiramide, when $R_{11}$=H, $R_{12}$=2-propenyl, $R_{13}$=amino, $R_{14}$=4-hydroxyphenyl, Z=S, the compound is known as Cefprozil, when $R_{11}$=H, $R_{12}$=$CH_3$, $R_{13}$=amino, $R_{14}$=(IIIaE), Z=S, the compound is known as Cefroxadine, when $R_{11}$=H, $R_{12}$=$CH_3$, $R_{13}$=amino, $R_{14}$=phenyl, Z=S, the compound is known as Cephalexin, when $R_{11}$=H, $R_{12}$=$CH_3$, $R_{13}$=(IIIaF) with $T_2$=$CH_3$, $R_{14}$=phenyl, Z=S, the compound is known as Cephaloglycin, when $R_{11}$=H, $R_{12}$=$CH_3$, $R_{13}$=amino, $R_{14}$=(IIIaE), Z=S, the compound is known as Cephadrine, when $R_{11}$=H, $R_{12}$=Cl, $R_{13}$=amino, $R_{14}$=phenyl, Z=C, the compound is known as Loracarbef, when $R_{11}$=(IIIaF) with $T_2$=tert-butyl, $R_{12}$=$CH_3$, $R_{13}$=amino, $R_{14}$=phenyl, Z=S, the compound is known as Pivcefalexin, when $R_{11}$=H, $R_{12}$=(IIIaC), $R_{13}$=OH, $R_{14}$=phenyl, Z=S, the compound is known as Cefamandole.

In class IIIb:

when $R_{15}$=$(CH_3)_3CCOOCH_2OCO-$, $R_{16}$=$NH_2COOCH_2-$, $R_{17}$=$C_2H_5$, X=CH, Y=C, the compound is known as Cefcapene Pivoxil, when $R_{15}$=$COO^-$, $P_{16}$=(IIIbL), $R_{17}$=methoxyl, X=Y=N, the compound is known as Cefclidin, when $R_{15}$=COOH, $R_{16}$=$-CH=CH_2$, $R_{17}$=OH, X=N, Y=C, the compound is known as Cefdinir, when $R_{15}$=COOH, $R_{16}$=(IIIbA), $R_{17}$=$OCH_3$, X=N, Y=C, the compound is known as Cefditoren, when $R_{15}$=$COO^-$, $R_{16}$=(IIIbM), $R_{17}$=$OCH_3$, X=N, Y=C, the compound is known as Cefepime, when $R_{15}$=COOH, $R_{16}$=$CH_3$, $R_{17}$=$OCH_3$, X=N, Y=C, the compound is known as Cefetamet, when $R_{15}$=COOH, $R_{16}$=$-CH=CH_2$, $R_{17}$=$-OCH_2OCOOH$, X=N, Y=C, the compound is known as Cefixime, when $R_{15}$=COOH, $R_{16}$=(IIIbC), $R_{17}$=$OCH_3$, X=N, Y=C, the compound is known as Cefmenoxime, when $R_{15}$=$COO^-$, $R_{16}$=(IIIbN), $R_{17}$=OCH, X=Y=N, the compound is known as Cefozopran, when $R_{15}$=$(CH_3)_2CHOCOOCH(CH_3)OCO-$, $R_{16}$=$C_2H_5$, $R_{17}$=$OCH_3$, X=N, Y=C, the compound is known as Cefpodoxime Proxetil, when $R_{15}$=COOH, $R_{16}$=(IIIbD), $R_{17}$=$OCH_3$, X=N, Y=C, the compound is known as Cefteram, when $R_{15}$=COOH, $R_{16}$=H, $R_{17}$=$-CH_2COOH$, X=CH, Y=C, the compound is known as Ceftibuten, when $R_{15}$=COOH, $R_{16}$=(IIIBH), $R_{17}$=$OCH_3$, X=N, Y=C, the compound is known as Ceftriaxone, when $R_{15}$=COOH, $R_{16}$=(IIIbE), $R_{17}$=$OCH_3$, X=N, Y=C, the compound is known as Cefuzonam, when $R_{15}$=COOH, $R_{16}$=(IIIbF), $R_{17}$=$OCH_3$, X=N, Y=C, the compound is known as Cefodizime, when $R_{15}$=COOH, $R_{16}$=$CH_3COOCH_2-$, $R_{17}$=$OCH_3$, X=N, Y=C, the compound is known as Cefotaxime, when $R_{15}$=COOH, $R_{16}$=(IIIbG), $R_{17}$=$OCH_3$, X=N, Y=C, the compound is known as Ceftiofur.

In class IIIc:

when $R_{18}$=(IIIcD), $R_{19}$=(IIIcH), the compound is known as Cefotiam, when $R_{18}$=(IIIcE), $R_{19}$=H, the compound is known as Ceftizoxime, when $R_{18}$=(IIIcF), $R_{19}$=(IIIcN), the compound is known as Cefazolin, when $R_{18}$=(IIIcG), $R_{19}$=(IIIcM), the compound is known as Ceforanide, when $R_{18}$=(IIIcA), $R_{19}$=(IIIcL), the compound is known as Cefminox, when $R_{18}$=(IIIcB), $R_{19}$=$CH_3COOCH_2-$, the compound is known as Cephalosporin C.

In Class IVa:

when $R_{20}$=(IVaF) and $R_{21}$=H, the compound is known as Amdinocillin, when $R_{20}$=(IVaF) and $R_{21}$=(IIIaF) with $T_2$=tert-butyl, the compound is known as Amdinocillin Pivoxil, when $R_{20}$=(IVaA) and $R_{21}$=H, the compound is known as Amoxicillin, when $R_{20}$=(IVaB) and $R_{21}$=H, the compound is known as Ampicillin, when $R_{20}$=(IVaM) and $R_{21}$=H, the compound is known as Apalcillin, when $R_{20}$=(IVaG) and $R_{21}$=H, the compound is known as Aspoxicillin, when $R_{20}$=(IVaB) and $R_{21}$=$-CH(CH_3)OCOOC_2H_5$, the compound ia known as Bacampicillin, when $R_{20}$=(IVaE) and $R_{21}$=H, the compound is known as Cyclacillin, when $R_{20}$=(IVaC) and $R_{21}$=H, the compound is known as Epicillin, when $R_{20}$=(IVaC) and $R_{21}$=H, the compound is known as Hetacillin, when $R_{20}$=(IVaC) and $R_{21}$=(IVaS), the compound is known as Lenampicillin, when $R_{20}$=(IVa) and $R_{21}$=H, the compound is known as Mezlocillin, when $R_{20}$=(IVaD) and $R_{21}$=(IVaR), the compound is known as Penethamate Hydroiodide, when $R_{20}$=(IVaP) and $R_{21}$=H, the compound is known as Penicillin N, when $R_{20}$=(IVaB) and $R_{21}$=(IIIaF) with $T_2$=tert-butyl, the compound is known as Pivampicillin, when $R_{20}$=(IVaN) and $R_{21}$=H, the compound is known as Quinacillin, when $R_{20}$=(IVaB) and $R_{21}$=(IVaU), the compound is known as Sultamicillin, when $R_{20}$=(IVaB) and $R_{21}$=(IVaT), the compound is known as Talampicillin.

In class IVb:

when $R_{22}$=$CH_3$, $R_{23}$=(IVbA), the compound is known as Meropenem, when $R_{22}$=H, $R_{23}$=(IVbC), the compound is known as Panipenem, when $R_{22}$=H, $R_{23}$=(IVbD), the compound is known as Imipenem.

In class IVc:

when $R_{23}$=$CH_3$, $R_{34}$=$CH_3$, $R_{35}$=H, $R_{36}$=$CH_3$, the compound is known as Aztreonam, when $R_{33}$=H, $R_{34}$=H, $R_{35}$=$-CH_2OCONH_2$, $R_{36}$=H, the compound is known as Carumonam.

In class V:

when $R_{24}$=Br, the compound is known as Brodimoprim, when $R_{24}$=OCH$_3$, the compound is known as Trimethoprim, when $R_{24}$=CH$_3$OCH$_2$CH$_2$O—, the compound is known as Tetroxoprim.

In class VI:

when $R_{25}$=(VID) the compound is known as Furaltadone, when $R_{25}$=(VIC) the compound is known as Furazolium chloride, when $R_{25}$=(VIE) the compound is known as Nifurfoline, when $R_{25}$=(VIA) the compound is known as Nifurpirinol, when $R_{25}$=(VIB) the compound is known as Nifurprazine.

In class VII:

when $R_{26}$=H, the compound is known as Sulfanilamide, when $R_{26}$=benzoyl, the compound is known as Sulfabenzamide, when $R_{26}$=acetyl, the compound is known as Sulfacetamide, when $R_{26}$=3-methyl-2-butenoyl, the compound is known as Sulfadicramide, when $R_{26}$=carbamoyl, the compound is known as Sulfanilylurea, when $R_{26}$=NH$_2$C(S)—, the compound is known as Sulfathiourea, when $R_{26}$=2-pyridinyl, the compound is known as Sulfapyridine, when $R_{26}$=pyrazinyl, the compound is known as Sulfapyrazine, when $R_{26}$=2-pyrimidinyl, the compound is known as Sulfadiazine, when $R_{26}$=2-thiazolyl, the compound is known as Sulfathiazole, when $R_{26}$=salicyl-4-yl, the compound is known as 4-sulphanilamido salicylic acid, when $R_{26}$=6-chloro-pyridazinyl-3-yl, the compound is known as Sulfachlorpyridazine, when $R_{26}$=1-ethyl-1,2-dihydro-2-oxo-pyrimidin-4-yl, the compound is known as Sulfacytine, when $R_{26}$=5,6-dimethoxy-pyrimidin-4-yl, the compound is known as Sulfadoxine, when $R_{26}$=2,6-dimethoxy-pyrimidin-4-yl, the compound is known as Sulfadimethoxine, when $R_{26}$=4-methyl-pyrimidin-2-yl, the compound is known as Sulfamerazine, when $R_{26}$=5-methoxy-pyrimidin-2-yl, the compound is known as Sulfameter, when $R_{26}$=4,6-dimethyl-pyrimidin-2-yl, the compound is known as Sulfamethazine when $R_{26}$=6-methoxy-2-methyl-pyrimidin-4-yl, the compound is known as Sulfamethomidine, when $R_{26}$=5-methyl-pyrimidin-2-yl, the compound is known as Sulfaperine, when $R_{26}$=2,6-dimethylpyrimidin-4-yl, the compound is known as Sulfisomidine, when $R_{26}$=3-methoxy-pyrazin-2-yl, the compound is known as Sulfalene, when $R_{26}$=6-methoxy-pyridazin-3-yl, the compound is known as Sulfamethoxypyridazine, when $R_{26}$=4,6-diethyl-1,3,5-triazin-2-yl, the compound is known as Sulfasymazine, when $R_{26}$=5-ethyl-1,3,4-thiadiazol-2-yl, the compound is known as Sulfaethidole, when $R_{26}$=5-methyl-1,3,4-thiadiazol-2-yl, the compound is known as Sulfamethizole, when $R_{26}$=4-methoxy-1,2,5-thiadiazol-3-yl, the compound is known as Sulfametrole, when $R_{26}$=4-methyl-thiazol-2-yl, the compound is known as Sulfamethylthiazole, when $R_{26}$=3-methyl-isothiazol-5-yl, the compound is known as Sulfasomizole, when $R_{26}$=4,5-dimethyl-oxazol-2-yl, the compound is known as Sulfamoxole, when $R_{26}$=3,4-dimethy-isoxazol-5-yl, the compound is known as Sulfisoxazole, when $R_{26}$=4,5-dimethyl-2-oxazolylaminoiminomethyl, the compound is known as Sulfaguanol, when $R_{26}$=5-methyl-isoxazol-3-yl, the compound is known as Sulfamethoxazole, when $R_{26}$=1-phenyl-1H-pyrazol-5-yl, the compound is known as Sulfaphenazole, when $R_{26}$=4-methylamino sulphonylphenyl, the compound is known as 4'-(methylsulfamoyl)sulfanilanilide, when $R_{26}$=4-aminosulphonylphenyl, the compound is known as N$^{-4}$ sulfanilylsulfanilamide, when $R_{26}$=3,4-dimethylbenzoyl, the compound is known as N-sulfanyl-3,4-xylamide, when $R_{26}$=4-isopropoxybenzoyl, the compound is known as Sulfaproxyline.

In class VIII:

when $R_{27}$=H, $R_{28}$=2,4-diamino-6-carboxyphenyl, the compound is known as Sulfachrysoidine, when $R_{27}$=H, $R_{28}$=2,4-diaminophenyl, the compound is known as Sulfamidochrysoidine, when $R_{27}$=4,6-dimethyl-pyrimidin-2-yl, $R_{28}$=3-carboxy-4-hydroxyphenyl, the compound is known as Salazo sulfadimidine.

In class IX:

when $R_{29}$=OH, $R_{30}$=COOH, the compound is known as p-Aminosalicylic acid, when $R_{29}$=OH, $R_{30}$=hydrazinecarbonyl, the compound is known as p-Aminosalicylhydrazide, when $R_{29}$=OH, $R_{30}$=phenoxycarbonyl, the compound is known as Phenylaminosalicylate, when $R_{29}$=H, $R_{30}$=4-(amino)phenylsulphinyl, the compound is known as 4,4'-Sulphinyldianiline.

In class X:

when $R_{31}$=amino, $R_{32}$=4-(hydroxyethylamino)phenyl, the compound is known as 2-p-Sulfanilylanilino ethanol, when $R_{31}$=amino, $R_{32}$=—N=C(NH$_2$)$_2$, the compound is known as Sulfaguanidine, when $R_{31}$=NH$_2$CH$_2$—, $R_{32}$=amino, the compound is known as Mafenide, when $R_{31}$=benzylamino, $R_{32}$=amino, the compound is known as Benzylsulfamide, when $R_{31}$=amino, $R_{32}$=4-(carboxymethylamino)phenyl, the compound is known as Acediasulfone, when $R_{31}$=amino, $R_{32}$=4-(amino)phenyl, the compound is known as Dapsone, when $R_{31}$=amino, $R_{32}$=4-(carboxypropionylamino)phenyl, the compound is known as Succisulfone, when $R_{31}$=amino, $R_{32}$=4-(aminomethyl)phenyl, the compound is known as p-Sulfanilylbenzylamine, when $R_{31}$=amino, $R_{32}$=2-amino-thiazol-5-yl, the compound is known as Thiazolsulfone.

In class XI:
when $R_{52}$=$C_2H_5$, $R_{53}$=amino, M=S, the compound is known as Ethionamide,
when $R_{52}$=H, $R_{53}$=—NHNH$_2$, M=O, the compound is known as Isoniazid,
when $R_{52}$=$C_3H_7$, $R_{53}$=amino, M=S, the compound is known as Protionamide,
when $R_{52}$=H, $R_{53}$=(XIA), M=O, the compound is known as Sulfoniazide,
when $R_{52}$=H, $R_{53}$=(XIB), M=O, the compound is known as Verazide,
when $R_{52}$=H, $R_{53}$=(XIC), M=O, the compound is known as Opiniazide,
when $R_{52}$=H, $R_{53}$=(XID), M=O, the compound is known as Salinazid,
when $R_{52}$=H, $R_{53}$=(XIE), M=O, the compound is known as Furonazide,
when $R_{52}$=H, $R_{53}$=(XIF), M=O, the compound is known as Glyconiazide.

In class XII:
when $R_{37}$=Cl, the compound is known as Clindamycin,
when $R_{37}$=OH, the compound is known as Lincomycin.

In class XIIIa:
when $R_{38}$=acetyl, $R_{39}$=isovaleryl, $R_{40}$=H, $R_{41}$=H, the compound is known as Josamycin,
when $R_{38}$=propionyl, $R_{39}$=propionyl, $R_{40}$=H, $R_{41}$=H, the compound is known as Midecamycin $A_1$,
when $R_{38}$=H, $R_{39}$=butyryl, $R_{40}$=propionyl, $R_{41}$=H, the compound is known as Rokictamycin,
when $R_{38}$=H, $R_{39}$=H, $R_{40}$=H, $R_{41}$=(XIIIaB), the compound is known as Spiramycin I,
when $R_{38}$=acetyl, $R_{39}$=H, $R_{40}$=H, $R_{41}$=(XIIIaB), the compound is known as Spiramycin II,
when $R_{38}$=propionyl, $R_{39}$=H, $R_{40}$=H, $R_{41}$=(XIIIaB), the compound is known as Spiramycin III,
when $R_{38}$=H, $R_{39}$=isovaleryl, $R_{40}$=H, $R_{41}$=H, the compound is known as Leucomycin.

In class XIIIb:
when $R_{47}$=H, $R_{48}$=H, W=—N(CH$_3$)CH$_2$—, the compound is known as Azithromycin,
when $R_{47}$=CH$_3$, $R_{48}$=H, W=carbonyl, the compound is known as Clarithromycin,
when $R_{47}$=H, $R_{48}$=H, W=carbonyl, the compound is known as Erythromycin,
when $R_{47}$=H, $R_{48}$ and W for together (XIIIbA), the compound is known as Dirithromycin.

In class XIVa:
when $R_{42}$=OH, $R_{43}$=(S)-4-amino-2-hydroxybutyryl, $R_{44}$=OH, $R_{45}$=OH, the compound is known as Amikacin,
when $R_{42}$=amino, $R_{43}$=(R)-4-amino-2-hydroxy butyryl, $R_{44}$=H, $R_{45}$=H, the compound is known as Arbekacin,
when $R_{42}$=amino, $R_{43}$=H, $R_{44}$=H, $R_{45}$=H, the compound is known as Dibekacin,
when $R_{42}$=amino, $R_{43}$=H, $R_{44}$=OH, $R_{45}$=H, the compound is known as Tobramycin.

In class XIVb:
when $R_{46}$=—CH$_2$OH, the compound is known as Dihydrostreptomycin,
when $R_{46}$=—CHO, the compound is known as Streptomycin.

In class XIVc:
when $R_{49}$=CH$_3$, the compound is known as Spectinomycin,
when $R_{49}$=C$_4$H$_9$, the compound is known as Trospectomycin.

In class XIVd:
when $R_{50}$H, $R_{51}$=(XIVdA), the compound is known as Micronomicin,
when $R_{50}$=C$_2$H$_5$, $R_{51}$=3-amino-6-(aminomethyl)-3,4-dihydro-2H-pyran-2-yl, the compound is known as Netilmicin,
when $R_{50}$=H, $R_{51}$=3-amino-6-(aminomethyl)-3,4-dihydro-2H-pyran-2-yl, the compound is known as Sisomicin.

In class XIVe:
when $R_{60}$=amino, $R_{61}$=(XIVeA) the compound is known as Neomycin,
when $R_{60}$=OH, $R_{61}$=(XIVed) the compound is known as Paromycin,
when $R_{60}$=amino, $R_{61}$=H, the compound is known as Ribostamycin.

In class XV:
when $R_{54}$=CH$_3$, the compound is known as Rifampin,
when $R_{54}$=cyclopentyl, the compound is known as Rifapentine.

In class XVIa:
when $X_b$=N, $R_{55}$=H, $R_{56}$=OH, $R_{57}$=β-D-ribofuranosyl, the compound is known as Inosine,
when $X_b$=N, $R_{55}$=amino, $R_{56}$=H, $R_{57}$=4-acetoxy-3-(acetoxymethyl)1-butyl, the compound is known as Famcyclovir,
when $X_b$=C, $R_{55}$=H, $R_{56}$=amino, $R_{57}$=β-D-ribofuranosyl, the compound is known as Tubercidin.

In class XVIb:
when $R_{58}$=H, $R_{59}$=β-D-(2,3-dideoxy)ribo furanosyl, the compound is known as Didanosine,
when $R_{58}$=amino, $R_{59}$=CH$_2$OCH$_2$CH$_2$OH, the compound is known as Acyclovir,
when $R_{58}$=amino, $R_{59}$=CH$_2$OCH$_2$CH$_2$OCOCH(NH$_2$)CH(CH$_3$)$_2$, the compound is known as Valacyclovir,
when $R_{58}$=amino, $R_{59}$=CH$_2$OCH(CH$_2$OH)CH$_2$OH, the compound is known as Gancyclovir.

The following compounds are preferred:
In class I:
when $R_1$=H, $R_2$=H, $R_3$=CH$_3$, $R_4$=OH, $R_5$=H, the compound is known as Doxycycline,
when $R_1$=H, $R_2$=OH, $R_3$=H, $R_4$=OH, $R_5$=H, the compound is known as Oxytetracycline,
when $R_1$=H, $R_2$=OH, $R_3$=CH$_3$, $R_4$=H, $R_5$=H, the compound is known as Tetracycline.

In class II:
when $R_6$=cyclopropyl, $R_7$=H, $R_8$=F, $R_9$=(IIA) with M=H, $R_{10}$=H, X=Y=C, the compound is known as Ciprofloxacin,
when $R_6$=C$_2$H$_5$, $R_7$=H, $R_8$=H, $R_9$=CH$_3$, $R_{10}$=free valence, X=N, Y=C, the compound is known as Nalidixic acid,
when $R_6$=C$_2$H$_5$, $R_7$=H, $R_8$=F, $R_9$=(IIA) with M=H, $R_{10}$=H, X=Y=C, the compound is known as Norfloxacin,
when $R_6$ with $R_{10}$ form the bivalent radical (IIN), $R_7$=H, $R_8$=F, $R_9$=(IIA) with M=CH$_3$, X=Y=C, the compound is known as Ofloxacin.

In class IIIa:

when $R_{11}$=H, $R_{12}$=Cl, $R_{13}$=amino, $R_{14}$=phenyl, Z=S, the compound is known as Cefaclor, when $R_{11}$=H, $R_{12}$=CH$_3$, $R_{13}$=amino, $R_{14}$=phenyl, Z=S, the compound is known as Cephalexin, when $R_{11}$=H, $R_{12}$=(IIIaC), $R_{13}$=OH, $R_{14}$=phenyl, Z=S, the compound is known as Cefamandole.

In class IIIb:

when $R_{15}$=COOH, $R_{16}$=ethenyl, $R_{17}$=—OCH$_2$OCOOH, X=N, Y=C, the compound is known as Cefixime, when $R_{15}$=(CH$_3$)$_2$CHOCOOCH(CH$_3$)OCO—, $R_{16}$=C$_2$H$_5$, $R_{17}$=OCH$_3$, X=N, Y=C, the compound is known as Cefpodoxime Proxetil, when $R_{15}$=COOH, $R_{16}$=(IIIbF), $R_{17}$=OCH$_1$, X=N, Y=C, the compound is known as Cefodizime.

In class IIIc:

when $R_{18}$=(IIIcF), $R_{19}$=(IIIcN), the compound is known as Cefazolin.

In class IVa:

when $R_{20}$=(IVaA) and $R_{21}$=H, the compound is known as Amoxicillin, when $R_{20}$=(IVaB) and $R_{21}$=H, the compound is known as Ampicillin, when $R_{20}$=(IVaM) and $R_{21}$=H, the compound is known as Apalcillin.

In class IVb:

when $R_{22}$=H, $R_{23}$=(IVbD), the compound is known as Imipenem.

In class IVc:

when $R_{33}$=CH$_3$, $R_{34}$=CH$_3$, $R_{35}$=H, $R_{36}$=CH$_3$, the compound is known as Aztreonam.

In class V:

when $R_{24}$=OCH$_3$, the compound is known as Trimethoprim.

In class VI:

when $R_{25}$=(VIE) the compound is known as Nifurfoline.

In class VII:

when $R_{26}$=5-methyl-isoxazol-3-yl, the compound is known as Sulfamethoxazole.

In class X:

when $R_{31}$=amino, $R_{32}$=4-(amino)phenyl, the compound is known as Dapsone.

In class XI:

when $R_{52}$=C$_2$H$_5$, $R_{53}$=amino, M=S, the compound is known as Ethionamide;

when $R_{52}$=H, $R_{53}$=—NHNH$_2$, M=O, the compound is known as Isoniazid.

In class XIIIb:

when $R_{47}$=H, $R_{48}$=H, W=—N(CH$_3$)CH$_2$—, the compound is known as Azithromycin, when $R_{47}$=H, $R_{48}$=H, W=carbonyl, the compound is known as Erythromycin, when $R_{47}$=CH$_3$, $R_{48}$=H, W=carbonyl, the compound is known as Clarithromycin.

In class XIVa:

when $R_{42}$=OH, $R_{43}$=(S)-4-amino-2-hydroxybutyryl, $R_{44}$=OH, $R_{45}$=OH, the compound is known as Amikacin, when $R_{42}$=amino, $R_{43}$=H, $R_{44}$=OH, $R_{45}$=H, the compound is known as Tobramycin.

In class XIVb:

when $R_{46}$=—CHO, the compound is known as Streptomycin.

In class XIVc:

when $R_{49}$=CH$_3$, the compound is known as Spectinomycin.

In class XIVd:

when $R_{50}$=C$_2$H$_5$, $R_{51}$=3-amino-6-(aminomethyl)-3,4-dihydro-2H-pyran-2-yl, the compound is known as Netilmicin.

In class XIVe:

when $R_{60}$=amino, $R_{61}$=(XIVeA) the compound is known as Neomycin.

In class XV:

when $R_{54}$=CH$_3$, the compound is known as Rifampin.

In class XVIa:

when $X_b$=N, $R_{55}$=H, $R_{56}$=OH, $R_{57}$=β-D-ribofuranosyl, the compound is known as Inosine, when $X_b$=N, $R_{55}$=amino, $R_{56}$=H, $R_{57}$=4-acetoxy-3-(acetoxymethyl)1-butyl, the compound is known as Famcyclovir.

In class XVIb:

when $R_{58}$=H, $R_{59}$=β-D-(2,3-dideoxy)ribo furanosyl, the compound is known as Didanosine, when $R_{58}$=amino, $R_{59}$=CH$_2$OCH$_2$CH$_2$OH, the compound is known as Acyclovir, when $R_{58}$=amino, $R_{59}$=CH$_2$OCH$_2$CH$_2$OCOCH(NH$_2$)CH(CH$_3$)$_2$, the compound is known as Valacyclovir, when $R_{58}$=amino, $R_{59}$=CH$_2$OCH(CH$_2$OH)CH$_2$OH, the compound is known as Gancyclovir.

In class XVII:

O-2-amino-2-deoxy-α-D-glucopyranosyl-(1→4)-O-[3-deoxy-3-(methylamino)-α-D-xylopyranosyl-(1→6)]-2-deoxy-D-streptamine (Gentamycin A), (S)-2-amino-5-[(aminoiminomethyl)amino]pentanoic acid (Arginine), (+)-2,2'-(ethylendiimino)di-1-butanol (Ethambutol), 1-amino adamantan (Amantadine), 2',3'-dideoxy-cytidine (zalcitabine), Pyrazinamide, Morphazinamide, Teicoplanin, Vancomycin, Metronidazole A further object of the invention are also the nitrate salts of antimicrobial, preferably antiviral, antifungal and antibacterial agents, or their pharmaceutical compositions, for the preparation of medicaments, excluding the nitrate salts of Erythromycin, Isoniazid, Pyrazinamide, Metronidazole, Acyclovir.

In the present invention can be used also the nitrate salts of the corresponding nitrooxy derivatives of the above listed antimicrobic agents, said nitrooxy derivatives characterized in that in their molecules there are one or more, preferably one, substituents having the general formula (I-N)

—B—(W)$_p$—ONO$_2$    (I-N)

wherein:

p is 1 or 0;

B=—T$_B$—Y—$_{BI}$— wherein T$_B$ e T$_{BI}$ are same or different; T$_B$ is a chemical function covalently linked to the chemical or reactive function of the drug molecule and is (CO) or X, wherein X=O, S, NH, with the condition that X=(CO) when the reacting function of the drug is OH or NH$_2$ or SH; T$_B$ is X when the reacting function of the drug is a carboxyl group;

T$_{BI}$=(CO)$_{tx}$ or (X)$_{txx}$, wherein tx and tax are 0 or 1; with the condition that tx=1 when txx=0, tx=0 when txx=1; X is as above defined;

Y is a bivalent linking bridge chosen between the following structures:

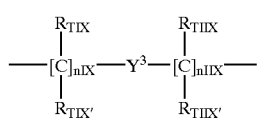
(II-Y)

wherein:
nIX is an integer comprised between 0 and 3, preferably is 1;
nIIX is an integer comprised between 0 and 3, preferably is 1;
$R_{TIX}$, $R_{TIX'}$, $R_{TIIX}$, $R_{TIIX'}$, same or different each from the other, are H or linear or branched $C_1$–$C_4$ alkyl; preferably $R_{TIX}$, $R_{TIX'}$, $R_{TIIX}$, are H.
$Y^3$ is a ring containing at least one salifiable nitrogen atom; preferably Y is an heterocyclic ring containing one or two nitrogen atoms, the ring saturated, unsaturated or aromatic, having preferably 5 or 6 atoms.

An alkylene group R' wherein R' is a linear or branched $C_1$–$C_{20}$ alkyl, preferably a $C_2$–$C_6$ alkyl, optionally substituted with one or more of the following groups: —NHCOR$_{3Y}$, wherein R$_{3Y}$ is a linear or branched $C_1$–$C_5$ alkyl, —NH$_2$, —OH;

A cycloalkylene ring $C_5$–$C_7$, optionally substituted with R', being R' as above defined, wherein one or more C atoms of the cycloalkylene can be optionally substituted with heteroatoms;

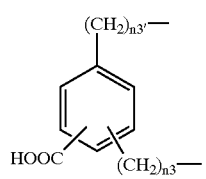
(III-Y)

wherein n3 is an integer from 0 to 3 and n3' is an integer from 1 to 3;

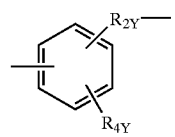
(IV-Y)

wherein n3 and n3' have the meanings above indicated;

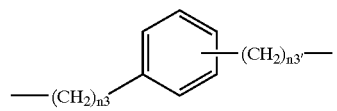
(V-Y)

wherein:
$R_{4Y}$ is OH, H, alcoxy $R_{5Y}O$— wherein $R_{5Y}$ is a linear or branched or cyclo $C_1$–$C_{10}$ alkyl, preferably $R_{5Y}$ is methyl;
$R_{2Y}$ is a linear or branched alkenylene $C_2$–$C_{10}$ containing one or more double bonds, preferably $R_{2Y}$ is an ethenylene group (—CH=CH—);

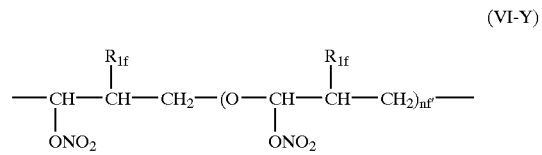
(VI-Y)

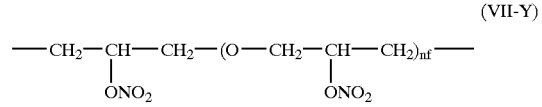
(VII-Y)

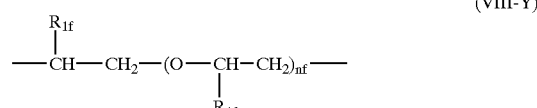
(VIII-Y)

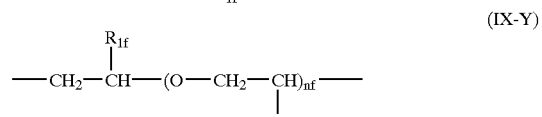
(IX-Y)

wherein $R_{1f}$=H, CH$_3$ and nf is an integer from 0 to 6; preferably from 0 to 4;

W of formula (I-N) is the bivalent radical —T$_c$—Y$_T$- wherein:
$T_c$=(CO) when $t_x$=0, $T_c$=X when $t_{xx}$=0;
with the proviso that in formula (I-N) when p=1 $Y_T$ is different from Y and in the bivalent radical B:
Y is R' as above defined having a substituent NHCOR$_{3Y}$, preferably R' is a $C_2$ saturated alkyl and R$_{3Y}$ is CH$_3$; T$_a$=S; T$_{B1}$ is —CO—; preferably Y is —CH$_2$—CH(NHCOCH$_3$)— and B in formula (I-N) preferably has the following structure:

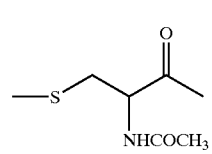
(X-Y)

or

Y is a bivalent radical of formula (V-Y), wherein $R_{4Y}$ is OR$_{5Y}$ and R$_{5Y}$ is preferably CH$_3$, R$_{2Y}$ is the group —CH=CH—; preferably Y has the following formula

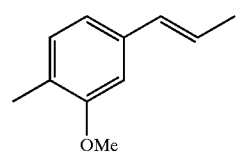
(XI-Y)

Preferably $Y^3$ in formula (II-Y) is selected from the following bivalent radicals:

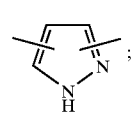
(Y1)

-continued (Y2) 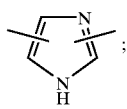

(Y3) 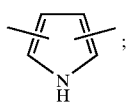

(Y4) 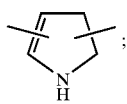

(Y5) 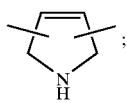

(Y6) 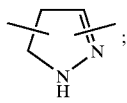

(Y7) 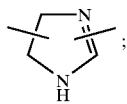

(Y8) 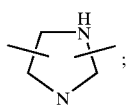

(Y9) 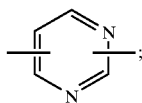

(Y10) 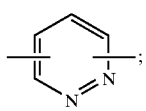

(Y11) 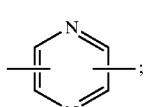

(Y12) 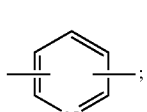

(Y13) 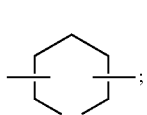

(Y14) 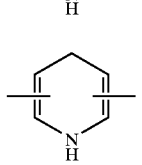

-continued (Y15) 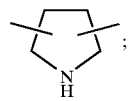

Preferably $Y^3$ is a 6-membered aromatic ring containing one nitrogen atom, said ring having the two free valences in the following positions: 2,6; 2,3; 2,5.

The preferred of $Y^3$ is Y12 (pirydil) substituted at positions 2 and 6.

Y1 (pyrazole) can be 3,5-disubstituted.

A further object of the present invention are the nitrate salts of the nitrooxy derivatives of the antimicrobial above listed compounds, preferably having antiviral, antifungal and antibacterial activity, or their pharmaceutical compositions, for the preparation of medicaments, excluding the nitrate salts of the nitrooxy derivatives of Erythromycin, Isoniazid, Pyrazinamide, Metronidazole, Acyclovir when in formula (I-N) p=0.

The derivatives of antibacterial agents having in their molecules one or more of the substituencs of formula (I-N) can be prepared according to methods known in the art.

In general, if in the molecule of the drug, or in the bivalent radicals B or W of formula (I-N) there are more than one reactive groups COOH and/or Hx, X being as above defined, said reactive groups must be protected before the reaction according to the methods known in the art; for example as described in the volume by Th. W. Greene: "Protective groups in organic synthesis", Harward University Press, 1980.

Acyl halides are prepared according to the methods known in the prior art, for example by thionyl or oxalyl chloride, $P^{III}$ or $P^{V}$ halides in inert solvents under the reaction conditions, such as for example toluene, chloroform, DMF, etc.

1) When the reactive chemical function of the drug is a carboxyl group and p=0 in formula (I-N), the corresponding nitrooxy derivatives can be prepared by the following methods:

1.a) The acid RCOOH (wherein R is the drug radical) and an halogen alcohol derivative of formula HO—Y—Hal, wherein Y is as above defined and Hal is an halogen atom, for example Cl, Br, Iodine, may be coupled to produce the ester of formula (1/C) by treatment with a de-hydrating agent such as N,N'-carbonyldiimidazol (CDI), N-hydroxy-benzotriazol, and dicyclohexylcarbodiimide (DCC) in the presence of a condensation catalyst such as 4-dimethylaminopyridine (DMAP), in a solvent such as for example DMF, THF, chloroform etc. at a temperature in the range from −5° C. to 50° C.

(1/C)

RCOOH $\xrightarrow{\text{CDI, HO—Y—Hal}}$ R—CO—O—Y—Hal 1.b) Alternatively the acid RCOOH may first be converted into an alkali metal salt such as sodium or potassium salt and reacted with a dihalogenated derivative of general formula Y(Hal)$_2$, wherein Y and Hal are as above defined.

R—COONa+Hal—Y—Hal-------->R—CO—O—Y—Hal   (1/B)

1.c) Alternatively the acid may first be converted to the acyl chloride of formula R—CO—Cl (wherein R is the drug radical) and then is reacted with an halogena alcohol of formula HO—Y—Hal or a dial of formula HO—Y—OH, wherein y is as above defined and Hal is halogen (Cl, Br, I):

R—COCl+HO—Y—Hal--------->R—CO—O—Y—Hal     (1/A)

R—COCl+HO—Y—HO--------->R—CO—C—Y—OH     (1/A')

1.d) The acid RCOOH and a dihalogenide compound of formula Hal—Y—Hal, wherein Y and Hal are as above defined, may be coupled to form an ester in the presence of a base, in an organic solvent inert in the reaction conditions according to the following scheme:

RCOHal+Hal—Y—Hal---→R—COO—Y—Hal     (1/D)

1.e) When the compounds obtained in the herein above described reactions have formula R—COO—Y—Hal, the corresponding nitrooxyderivatives are obtained by reacting the compound R—CO—O—Y—Hal with $AgNO_3$ in an organic solvent such as acetonitrile, tetrahydrofuran according to the following scheme:

R—COO—Y—Hal+AgNO₃-------→R—COO—Y—ONO₂

1.f) When the compounds obtained in the herein above described reactions have the formula R—COO—Y—OH, the hydroxy group is firstly halogenated, for instance by means of $PBr_3$, $PCl_5$, $SOCl_2$, $PPh_3+I_2$, then reacted with $AgNO_3$ in an organic solvent such as acetonitrile, tetrahydrofuran.

2) When in formula (I-N) p=0, and the free valence of R is saturated with an hydroxy group, the methods of synthesis of the corresponding nitrooxy derivatives are the following:

2.a) The drug of formula R—OH and an halogenoacid of formula Hal—Y—COOH or an hydroxyacid of formula HO—Y—COOH, wherein Y and Hal are as above defined, may be coupled according to the reactions known in the art to produce the esters of formula (2/A) or (2/B), according to the following schemes:

R—OH—Hal—Y—COCl-----→R—OCO—Y—Hal     (2/A)

R—OH—Hal—Y—COCl-----→R—OCO—Y—OH     (2/B)

2.b) When the compounds obtained in the herein above described reactions have the formula R—OCO—Y—Hal or R—OCO—Y—OH, the corrresponding nitrooxy derivatives are obtained as described in 1.f and 1.e respectively.

3. When in formula (I-N) p=1 and the reactive group of the drug molecule is a carboxyl group, the methods of synthesis for obtaining the corresponding nitrooxy derivatives are the following ones:

3.a) The drug of formula RCOOH may first be converted to the acyl chloride of formula R—CO—CL (wherein R is the drug radical) and then is reacted with a compound of formula HX—Y—COOH according to the methods known in the art, to obtain a compound of formula R—CO—X—Y—COOH, that it is converted into the corresponding sodium salt and then reacted with a compound of formula Hal—YT—RY wherein Hal e $Y_T$ are as above defined and $R_{BY}$ is Cl, Br, Iodine, OH:

R—COHal+HX—Y—COOH---→R—CO—X—Y—COOH     (3.A)

R—CO—X—Y—COONa+Hal—Y$_T$—R$_8$---→R—CO—X—Y—CO—Y$_T$—R$_8$     (3.A')

When $R_{8Y}$=OH, the compound of formula (3.A') is halogenated as above described in 1.f); when $R_{8Y}$=Hal the compound of formula (3.A') is reacted with $AgNO_3$ in an organic solvent such as acetonitrile, tetrahydrofuran:

3.b) When $Y_T$ is a linear alkylene $C_4$, the acid compound of formula (3.A) is reacted with triphenylphosphine in the presence of an halogenating agent such as $CBr_4$ or N-bromosuccinimide in tetrahydrofuran to give directly the compound of formula (3.A') wherein $R_{BY}$=Br, said compound is then converted into the corresponding nitrooxy derivative as described under i.e.

4) When in formula (I-N) p=1 and the reactive group of the antibacterian drug is an hydroxy group, the methods of synthesis for obtaining the corresponding nitrooxy derivatives are the following ones:

4.a) The drug of formula R—OH and an acyl halogenide of formula HX—Y—COHal wherein Y, X and Hal are as above defined, may be coupled according to the methods known in the art to produce the ester of formula of formula R—O—CO—Y—XH (4/A), that is then reacted with a compound of formula $R_{8Y}$—$Y_T$—COHal wherein $R_{8Y}$ and $Y_T$ are as above defined.

R—OH+HX—Y—COCl---→R—O—CO—Y—XH     (4/A)

R—O—CO—Y—XH+R$_8$—Y$_T$CO—Hal--→R—O—CO—Y—X—CO—Y$_T$—R$_{8Y}$     (4A')

4.b) Alternatively, the drug R—OH is reacted with a compound of formula HX—Y—COOH, wherein X and Y are as above defined, in the presence of dicyclohexylcarbodiimide as described under 1.a, to obtain a compound of formula R—O—CO—Y—XH, that is then reacted with a compound of formula $R_{8Y}$—$Y_T$—COCl wherein $R_{8Y}$ and $Y_T$ are as above defined, to give the following compound: R—O—CO—Y—X—CO—$Y_T$—$R_{8Y}$ (4/B) When $R_{8Y}$=OH the compound corresponding to the formula (4/B) or (4a') is halogenated as above described under 1.f); when $R_8$=Hal the compound of formula (4/B) is reacted with $AgNO_3$ in an organic solvent such as acetonitrile, tetrahydrofuran.

The nitrooxy derivatives of the antibacterian agent can also by prepared according to the synthetic methods described in WO 95/30641 herein incorporated by reference.

In the salts or their compositions according to the present invention also one or more isomers, including optical isomers, when possible, of the above described antimicrobial compounds can be used.

The nitrate salts according to the present invention contain at least one nitrate ion mole/compound mole. Preferably the ratio nitrate ion moles/precursor moles is unitary. Salts having a higher molar ratio are obtained when in the molecule more aminic groups, sufficiently basic to be able to be salified, are present.

The salts of the present invention are formulated in the corresponding pharmaceutical compositions according to well known techniques in the prior art, together with the usual excipients; see for example the volume "Remington's Pharmaceutical Sciences 15a Ed."

The precursors of the salts belonging to the above mentioned classes are prepared according to the methods described in the Merck Index 14a Ed., herein incorporated by reference.

The nitrate salts of the antibacterial compounds are prepared by the following methods.

When the compound to be salified is available as free base soluble in an organic solvent, which preferably does not contain hydroxyl groups, for example acetonitrile, ethyl acetate, tetrahydrofuran, etc., the salt is prepared by dissolving the compound in the solvent at a concentration preferably equal to or higher than 10% w/v, adding the amount of concentrated nitric acid corresponding to the moles of salifiable aminic groups present in the compound. The nitric acid is preferably diluted in the same solvent. Preferably during and after the addition it is cooled at temperatures in the range 0° C.–20° C.

The product is generally recovered by filtration and washed with the solvent.

When the compound is not very soluble, or it is available under the form of a not very soluble salt in the above mentioned solvents, the corresponding mixtures with hydroxylated solvents can be used. Examples of such solvents are methyl alcohol, ethyl alcohol and water. The precipitation of the nitrate salt can be accelerated by diluting then the so obtained mixture, after the addition of nitric acid, with an apolar solvent.

When the starting compound is salified with hydrochloric acid, it is possible to prepare the nitrate salt by directly adding silver nitrate to the compound solution. After having filtered the silver chloride, the solution is concentrated and cooled for recovering the nitrate salt.

When the starting compound is a salt, the corresponding base can also be released by treatment with a saturated solution of sodium or potassium bicarbonate or carbonate, or with a diluted solution of sodium or potassium hydroxide. The base is then extracted with a suitable organic solvent (for example halogenated solvents, esters, ethers), which is then dried. The organic solution is evaporated and one proceeds according to the previous preparation methods, by dissolving the base in acetonitrile or in the other above mentioned solvents.

The compounds and compositions of the present invention can be used for systemic applications, for example they can be administered by os with formulations known in the prior art such as for example tablets or capsules, or by parenteral route, such as for example by intravenous or intramuscular administration in formulations in sterile apyrogenic physiological solution, optionally additioned with other excipients known in the prior art.

It is possible to use the nitrate salts of the present invention for topical applications, under the form of gels or creams, or by aerosol (by inhalation).

As said, the compounds of the invention are used in the therapy of the same pathologies for which the precursor antimicrobial agents ar used. However since the products of the invention show an improved activity, they can be used even at lower doses. This is advantageous since it allows to avoid the side effects mentioned above for precursors.

The following Examples are given with the only purpose to illustrate the invention and they are not limitative of the same.

EXAMPLES

Preparation Examples

Example 1

Preparation of the Cefalexine Nitrate Salt

A solution of Cefalexine hydrochloride (3 g, 13.02 mmoles) in a mixture of acetonitrile (150 ml) and tetrahydrofuran (150 ml) is treated with silver nitrate (2.22 g, 13.06 mmoles) sheltered from the light. It is left under stirring for 30 minutes at room temperature, then the silver chloride is filtered and the solution is concentrated at a reduced pressure up to the half of the initial volume. Ethyl ether (100 ml) is added and, after cooling at 5° C., the obtained solid is filtered. After drying 4.3 g of Cefalexine nitrate salt as amorphous solid are obtained. Yield 80%.

| Elementary analysis for $C_{16}H_{18}N_4O_7S$ | | | | |
|---|---|---|---|---|
| Calculated %: | C 46.83; | H 4.42; | N 13.65; | S 7.81 |
| Found %: | C 46.81; | H 4.44; | N 13.63; | S 7.80 |

Example 2

Preparation of the Clindamycin Nitrate Salt

The compound is prepared by starting from a solution of Clindamycin hydrochloride (3 g, 6.5 mmoles) in ethanol (100 ml) by addition of silver nitrate (1.12 g, 6.59 mmoles) and following the procedure reported in Example 1. Clindamycin nitrate salt as amorphous solid is obtained. Yield 70%.

| Elementary analysis for $C_{18}H_{34}ClN_3O_8S$: | | | | |
|---|---|---|---|---|
| Calculated %: | C 44.30; | H 7.02; | Cl 7.26; | N 8.61; S 6.57 |
| Found %: | C 44.32; | H 7.03; | Cl 7.23; | N 8.62; S 6.55 |

Example 3

Preparation of the Amoxicillin Nitrate Salt

The compound is prepared starting from a solution of Amoxicillin hydrochloride (2 g, 4.98 mmoles) in a mixture of acetonitrile (80 ml)/tetrahydrofuran (80 ml) by addition of silver nitrate (0.850 g, 5.0 mmoles), following then the procedure reported in Example 1. Amoxicillin nitrate as amorphous solid is obtained. Yield 78%.

| Elementary analysis for $C_{16}H_{20}N_4O_8S$: | | | | |
|---|---|---|---|---|
| Calculated %: | C 44.86; | H 4.71; | N 13.08; | S 7.48 |
| Found %: | C 44.89; | H 4.74; | N 13.11; | S 7.45 |

Example 4

Preparation of the Tetracycline Nitrate Salt

The compound is prepared by starting from a solution of Tetracycline hydrochloride (2 g, 4.16 mmoles) in methanol (100 ml) by adding silver nitrate (0.71 g, 4.17 mmoles), and following then the procedure reported in Example 1. Tetracycline nitrate salt as amorphous solid is obtained. Yield 60%.

| Elementary analysis for $C_{22}H_{25}N_3O_{11}$: | | | |
|---|---|---|---|
| Calculated %: | C 52.07; | H 4.97; | N 8.28; |
| Found %: | C 52.05; | H 4.99; | N 8.30; |

Example 5

Preparation of the Clarithromycin Nitrate Salt

To a solution of Clarithromycin (2 g, 2.67 mmoles) in a mixture of acetonitrile (50 ml) and chloroform (80 ml), cooled at 0° C., a 65% $HNO_3$ solution (0.2 ml) in acetonitrile (5 ml) is added. After the addition the mixture is let reach the room temperature and it is maintained under stirring for two hours. The solvent is evaporated at a reduced pressure. The residue is dissolved in chloroform (50 ml) and ethyl ether (50 ml) is added. It is cooled at 5° C. and the precipitate which separates is filtered. After drying 1.83 g (2.26 mmoles) of Clarithromycin nitrate salt as amorphous solid are obtained. Yield 80%.

| Elementary analysis for $C_{38}H_{78}N_2O_{16}$: | | | |
|---|---|---|---|
| Calculated %: | C 56.28 | H 8.70 | N 3.45 |
| Found %: | C 56.25 | H 8.72 | N 3.46 |

Example 6
Preparation of the Ciprofloxacin Nitrate Salt

Triethylamine (0.9 ml, 6.5 mmoles) is added to a suspension of Ciprofloxacin hydrochloride (2 g, 5.4 mmoles) in 200 ml of methylene chloride. The solution is maintained under stirring for 30 minutes. The solution is washed with water (100 ml), the organic phase is dried by sodium sulphate and under vacuum obtaining the corresponding Ciprofloxacin base (1.03 g). The substance is dissolved in a mixture of acetonitrile (60 ml)/tetrahydrofuran (50 ml). The solution is cooled with ice and treated with a solution (0.220 ml) of 65% nitric acid in acetonitrile (5 ml). After 30 minutes under cold stirring it is treated with ethyl ether. A solid is separated which is filtered, washed with ethyl ether and dried under vacuum. 1.2 g of Ciprofloxacin nitrate salt as amorphous solid are obtained. Yield 45%.

| Elementary analysis for $C_{17}H_{19}N_4O_6F$: | | | | |
|---|---|---|---|---|
| Calculated %: | C 51.78; | H 4.86; | N 14.21; | F 4.82 |
| Found %: | C 51.75; | H 4.84; | N 14.25; | F 4.80 |

Example 7
Preparation of the Sulfamethoxazole Nitrate Salt

The compound is prepared by starting from a Sulfamethoxazole solution (2 g, 7.9 mmoli) in methanol (100 ml), addition of a 65% nitric acid solution (0.500 ml) in acetonitrile (5 ml), following the procedure reported in Example 5. Sulfamethoxazole nitrate as amorphous solid is obtained. Yield 60%.

| Elementary analysis for $C_{10}H_{12}N_4O_6S$: | | | | |
|---|---|---|---|---|
| Calculated %: | C 37.97; | H 3.82; | N 17.71; | S 10.15 |
| Found %: | C 37.99; | H 3.83; | N 17.73; | S 10.13 |

Example 8
Preparation of the Trimethoprim Nitrate Salt

The compound is synthetized starting from a solution of Trimethoprim (1.5 g, 5.17 mmoles) in chloroform (80 ml), by adding a 65% nitric acid solution (0.360 ml) in acetonitrile (5 ml) and following then the procedure described in Example 5. Trimethoprim nitrate salt as amorphous solid is obtained. Yield 60%.

| Elementary analysis for $C_{14}H_{19}N_5O_6$: | | | |
|---|---|---|---|
| Calculated %: | C 47.59 | H 5.42 | N 19.82 |
| Found %: | C 47.57 | H 5.44 | N 19.83 |

Example 9
Preparation of the Pyrazinamide Nitrate Salt

The compound is prepared starting from a solution of Pyrazinamide (2 g, 16.24 mmoles) in a mixture of acetonitrile (30 ml)/tetrahydrofuran (30 ml), by adding a 65% nitric acid solution (1.2 ml) in acetonitrile (5 ml), following then the procedure described in Example 5. Pyrazinamide nitrate salt as amorphous solid is obtained. Yield 74%.

| Elementary Analysis for $C_5H_6N_4O_4$: | | | |
|---|---|---|---|
| Calculated %: | C 32.27 | H 3.25 | N 30.10 |
| Found %: | C 32.29 | H 3.24 | N 30.13 |

Example 10
Preparation of the Nifurfoline Nitrate Salt

The compound is prepared starting from a Nifurfoline solution (1 g, 2.96 mmoles) in a mixture of tetrahydrofuran (20 ml)/acetonitrile (20 ml), by adding a 65% nitric acid solution (0.210 ml) in acetonitrile (3 ml), and following then the procedure described in Example 5. Nifurfoline nitrate salt as amorphous solid is obtained. Yield 55%.

| Elementary analysis for $C_{13}H_{16}N_6O_9$: | | | |
|---|---|---|---|
| Calculated %: | C 39.01 | H 4.03 | N 20.99 |
| Found %: | C 32.03 | H 4.05 | N 21.01 |

Example 11
Preparation of Acyclovir Nitrate Salt

The compound is prepared starting from an Acyclovir solution (1 g, 4.44 mmoles) in a mixture of tetrahydrofuran (20 ml)/acetonitrile (20 ml), by adding a 65% nitric acid solution (0.310 ml) in acetonitrile (5 ml), and following then the procedure described in Example 5. Acyclovir nitrate salt as amorphous solid is obtained. Yield 60%.

| Elementary analysis for $C_8H_{12}N_6O_6$: | | | |
|---|---|---|---|
| Calculated %: | C 33.34 | H 4.20 | N 29.17 |
| Found %: | C 33.31 | H 4.22 | N 29.19 |

Example 12
Preparation of Metronidazole Nitrate Salt

The compound is prepared starting from a metronidazole solution (1 g, 5.84 mmoles) in a mixture of tetrahydrofuran (10 ml)/acetonitrile (15 ml) and by adding a 65% nitric acid solution (0.410 ml) in acetonitrile (3 ml), following then the procedure described in Example 5. Metronidazole nitrate salt as amorphous solid is obtained. Yield 70%.

| Elementary analysis for $C_6H_{10}N_4O_6$: | | | |
|---|---|---|---|
| Calculated %: | C 30.77 | H 4.30 | N 24.03 |
| Found %: | C 30.74 | H 4.28 | N 24.01 |

Example 13
Preparation of Erythromycin Nitrate Salt

The compound is prepared starting from an erythromycin solution (2 g, 2.72 mmoles) dissolved in a mixture of chloroform (30 ml)/acetonitrile (20 ml), by adding a 65% nitric acid solution (0.200 ml) in acetonitrile (5 ml), following then the procedure described in Example 5. Erythromycin nitrate as amorphous solid is obtained. Yield 83%.

| Elementary analysis: | | | |
|---|---|---|---|
| Calculated %: | C 55.76 | H 8.59 | N 3.51 |
| Found %: | C 55.79 | H 8.60 | N 3.53 |

Example 14
Preparation of the Cefazolin Nitrate Salt

The compound is prepared by adding to a Cefazolin solution (1.5 g, 3.3 mmoles) in methanol (50 ml) a 65% nitric acid solution (0.250 ml) in acetonitrile (5 ml) and following then the procedure reported in Example 5. Cefazolin nitrate as amorphous solid is obtained. Yield 60%.

| Elementary Analysis for $C_{14}H_{15}N_9O_7S_3$: | | | |
|---|---|---|---|
| Calculated: | C 32.49; | H 2.92; | N 24.36; | S 18.59 |
| Found: | C 32.48; | H 2.94; | N 24.37; | S 18.57 |

Example 15
Preparation of the Ampicillin Nitrate Salt

The compound is prepared startaing from an Ampicillin solution (2 g, 5.72 rmoles) in a mixture formed by acetonitrile (30 ml) and tetrahydrofuran (20 ml), by adding a 65% nitric acid solution (0.450 ml) in acetonitrile (5 ml) and following the procedure reported in Example 5. Ampicillin nitrate as amorphous solid is obtained. Yield 55%.

| Elementary analysis for $C_{16}H_{20}N_4O_7S$: | | | |
|---|---|---|---|
| Calculated: | C 46.60; | H 4.89; | N 13.58; | S 7.77 |
| Found: | C 46.56; | H 5.91; | N 13.59; | S 7.76 |

Pharmacological Examples
Dilution Test in vitro on Medium for Antibacterial Agents The capability to antagonize the arising of the microbial resistance of the nitrate salts of the antimicrobial compounds in comparison with that of the respective precursors has been evaluated.

Such activity has been determined by using the dilution method in vitro on culture medium as described by Sahm et al. (S. D. Sahm, J. A. Washington "Antibacterial susceptibility tests: dilution methods" in: Manual of Clinical Microbiology, ed. A. Balows, W. J. Hausler, Jr, K. L. Hermann, H. D. Isenberg, H. J. Shadomy, 1991, American Society for Microbiology). According to this method a concentration in aqueous solution of substance having antimicrobial activity able to inhibit the growth of some bacterial strains is determined. For the precursor the maximum concentration of the substance at which the microbial growth is still observed under the adopted experimental conditions is selected and the same concentration is used for the corresponding nitrate salt. The solvents and the necessary dilutions for preparing the strain substances of the antibiotics to be tested are prepared according to procedures standard and well known to the man skilled in the field (National Committee for Clinical Laboratory Standards, 1990 "Methods for dilution antimicrobial susceptibility tests for bacteria that grow aerobically. Approved standard M7-A2. National Committee for Clinical Laboratory Standards, Villanova, Pa.). Also the preparation of the culture medium is carried out according to standard procedures and the CAMH broth is used (Cation-adjusted Mueller-Hinton broth) (National Committee for Clinical Laboratory Standards, 1990, Methods for dilution antimicrobial susceptibility tests for bacteria that grow aerobically. Approved standard M7-A2. National Committee for Clinical Laboratory Standards, Villanova, Pa.).

The inoculation procedure is carried out according to standard procedures and the final concentration of the inoculum is of $5 \times 10^5$ CFU (colony forming unit)/ml. The used microorganisms have been *Escherichia Coli* (ATCC25922) and Staphylococcus Aureus (ATCC29213).

The test tubes are incubated at 35° C. for 20 hr before reading. The microbial growth, or the absence of the same, is determined in a qualitative way, with the naked eye and it indicates the microbial resistance or, respectively, the sensitivity to the antimicrobial agent. The results of the tests are reported in Tables 1 and 2, which show that the nitrate salt has an antimicrobial activity higher than that of the precursor.

Example 16

Synthesis of 1-Ethyl-6,8-difluoro-1,4-dihydro-7-(3-methyl-1-piperazinyl)-4-oxo-3-quinolincarboxylic acid 4-nitrooxybutyl ester nitrate salt

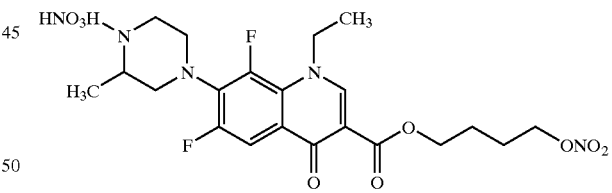

A) Synthesis of 1-Ethyl-6,8-difluoro-1,4-dihydro-7-(3-methyl-N-tert-butoxycarbonyl-1-piperazinyl)-4-oxo-3-quinolincarboxylic acid 4-bromobutyl ester To a stirred solution of 1-Ethyl-6,8-difluoro-1,4-dihydro-7-(3-methyl-1-piperazinyl)-4-oxo-3-quinolincarboxylic acid hydro chloride (504.14 mg, 1.3 mmoles) in 1,4-dioxane (2.6 ml) and NaOH 2M (1,3 ml), was added di-tert-butyl dicarbonate (306 mg, 1.4 mmoles) at 0° C. After stirring for 2 hours the suspension was filtered and the precipitate washed with 1,4-dioxane, dried to afford 1-Ethyl-6,8-difluoro-1,4-dihydro-7-(3-methyl-N-tert-butoxycarbonyl-1-piperazinyl)-4-oxo-3-quinolincarboxylic acid that was used without further purification.

To a suspension of 1-Ethyl-6,8-difluoro-1,4-dihydro-7-(3-methyl-N-tert-butoxycarbonyl-1-piperazinyl)-4-oxo-3- quinolin carboxylic acid and NaHCO₃ (11 mg, 1.3 mmoles) in DMF (10 ml) was added 1,4-dibromobutane (1.4 g, 6.5 mmoles).

The mixture was refluxed for 1 hour and, after cooling, were added in the order water and ethyl acetate. After separation of the phases the organic layer was washed with water, dried with sodium sulphate and evaporated under reduced pressure. The residue was purified by chromatography on silica gel eluting with ethyl acetate/n-hexane (v/v 2/1) to afford 1-Ethyl-6,8-difluoro-1,4-dihydro-7-(3-methyl-N-tert-butoxy carbonyl-1-piperazinyl)-4-oxo-3-quinolineecarboxylic acid 4-bromobutyl ester (380 mg, 0.65 mmoles) as an amorphous solid. Yield 50%.

B) Synthesis of 1-Ethyl-6,8-difluoro-1,4-dihydro-7-(3-methyl-1-piperazinyl)-4-oxo-3-quinolincarboxylic acid 4-nitrooxybutyl ester To a solution of 1-Ethyl-6,8-difluoro-1,4-dihydro-7-(3-methyl-N-tert-butoxycarbonyl-1-piperazinyl)-4-oxo-3-quinolin carboxylic acid 4-nitrooxybutyl ester (300 mg, 0.51 mmoles) in anhydrous acetonitrile (5 ml) was added silver nitrate (170 mg, 1 mmoles). The mixture was refluxed for 4 hours in the darkness.

The suspension was filtered and the filtrate washed with water (3×8 ml) and dried with sodium sulphate, then evaporated in vacuo.

The compound was deprotected by treating with trifluoroacetic acid (1 ml) at room temperature, in an inert atmosphere (N₂), for 1 hour. Trifluoroacetic acid was removed by evaporation under a reduced pressure and the residue was purified by chromatography on a weakly basic ion-exchange resin (Amberlyst® A-21) eluting with ethyl acetate to afford 1-ethyl-6,8-difluoro-1,4-dihydro-7-(3-methyl-1-piperazinyl)-4-oxo-3-quinolin carboxylic acid 4-nitrooxybutyl ester (150 mg, 0.32 mmoles) as an amorphous solid.

¹NMR (ppm): 8.25 (1H, s); 7.85 (1H, d); 4.52 (2H, t); 4.5–4.2 (4H, m); 3.4–2.8 (7H, m); 1.94–1.83 (4H, m); 1.48 (3H, m); 1.06 (3H, d).

C) Synthesis of 1-Ethyl-6,8-difluoro-1,4-dihydro-7-(3-methyl-1-piperazinyl)-4-oxo-3-quinolincarboxylic acid 4-nitrooxybutyl ester nitrate salt To a solution of 1-ethyl-6,8-difluoro-1,4-dihydro-7-(3-methyl-1-piperazinyl)-4-oxo-3-quinolincarboxylic acid 4-nitrooxy butyl ester (150 mg, 0.32 mmoles) in CH₂Cl₂ (2 ml) was added HCl—AcOEt 1 M (0.5 ml). After stirring for 1 hours at room temperature, the solvent was evaporated under reduced pressure and the residue dissolved in THF (4 ml) and silver nitrate (55 mg, 3.03 mmoles) was added. The mixture was stirred for 1 hour at room temperature, the suspension was filtered and the precipitate washed with THF, dried to afford 1-Ethyl-6,8-difluoro-1,4-dihydro-7-(3-methyl-1-piperazinyl)-4-oxo-3-quinolin carboxylic acid 4-nitrooxybutyl ester nitrate salt (150 mg) as an amorphous solid. Yield 88%.

Elementary Analysis:

|  | % C | % H | % N | % F |
|---|---|---|---|---|
| calculated: | 47.46 | 5.12 | 13.18 | 7.15 |
| found: | 47.50 | 5.10 | 13.10 | 7.20 |

Example 17

Synthesis of 1-Ethyl-6-fluoro-1,4-dihydro-4-oxo-7-(1-piperazinyl)-3-quinolinecarboxylic acid 4-nitrooxybutyl ester nitrate salt

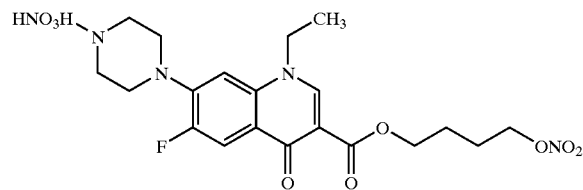

A) Synthesis of 1-Ethyl-6-fluoro-1,4-dihydro-4-oxo-7-(N-tert-butoxy carbonyl-1-piperazinyl-)-3-quinolinecarboxylic acid 4-bromobutyl ester To a solution of 1-Ethyl-6-fluoro-1,4-dihydro-7-(3-methyl-1-piperazinyl)-4-oxo-3-quinolincarboxylic acid hydro chloride (2.5 g, 7.8 mmoles) and KOH 2M (11.7 ml) in 1,4-dioxane (15 ml) was added di-tert-butyl dicarbonate (1.75 g, 8 mmoles), at −4° C. The mixture was stirred for 1 hour at 0° C., thereafter the cooling bath was removed and stirred until the temperature was risen to room temperature (about 1 hour). Water (15 ml) was added and, after cooling, the mixture was filtered and the precipitate was dried to afford 1-Ethyl-6-fluoro-1,4-dihydro-4-oxo-7-(N-tert-butoxycarbonyl-1-piperazinyl-)-3-quinoline carboxylic acid, that was used without further purification.

To a suspension of 1-Ethyl-6-fluoro-1,4-dihydro-4-oxo-7-(N-tert-butoxycarbonyl-1-piperazinyl-)-3-quinolinecarboxylic acid and 18-crown-6 (1,4,7,10,13-pentaoxacyclopentadecane) in anhydrous THF (20 ml) was added 1,4-dibromobutane (1.4 g, 6.5 mmoles) in an inert atmosphere (N₂).

The mixture was refluxed for 1 hour and, after cooling, water and ethyl acetate were added in the order.

After separation of the phases, the organic layer was washed with water, dried with sodium sulphate and evaporated Under reduced pressure.

The residue was purified by chromatography on silica gel eluting with ethyl acetate/n-hexane (v/v 2/1) to afford 1-Ethyl-6-fluoro-1,4-dihydro-7-(3-methyl-N-tert-butoxycarbonyl-1-pipera zinyl)-4-oxo-3-quinolinecarboxylic acid 4-bromobutyl ester 380 mg, 0.65 mmoles) as an amorphous solid. Yield 66%.

B) Synthesis of 1-Ethyl-6-fluoro-1,4-dihydro-4-oxo-7-(1-pipera zinyl)-3-quinolinecarboxylic acid 4-nitrooxybutyl ester nitrate salt To a solution of 1-Ethyl-6-fluoro-1,4-dihydro-4-oxo-7-(N-tert-butoxycarbonyl-1-piperazinyl-)-3-quinolincarboxylic acid 4-nitrooxybutyl ester (443.5 mg, 0.8 mmoles) in anhydrous acetonitrile (7 ml) was added silver nitrate (406 mg, 0.8 mmoles). The mixture was refluxed for 5 hours in the darkness, in an inert atmosphere (N₂). The suspension was filtered, the filtrate was evaporate in vacuo. The residue was dissolved in CH₂Cl₂ (10 ml; and the mixture was washed with water (5×10 ml) and anhydrified with sodium sulphate, the solvent was then evaporated under reduced pressure.

The compound was deprotected with trifluoroacetic acid (1.6 ml) at room temperature, in an inert atmosphere (N₂) for 1 hour. Trifluoroacetic acid was evaporated under reduced pressure and the residue was purified by chromatography on a weakly basic ion-exchange resin (Amberlyst® A-21) eluting with methanol to afford 1-Ethyl-6-fluoro-1,4-dihydro-4-oxo-7-(1-piperazinyl)-3-quinolinecarboxylic acid 4-nitrooxybutyl ester nitrate (306 mg, 0.7 mmoles) as a yellow amorphous solid.

$^1$H NMR (DMSO) ppm: 7.39 (5H, d); 7.03 (8H, d); 5.96 (2H, B); 4.58 (2H, m); 4.38 (2H, m); 4.18 (2H, m); 3.33 (4H, m); 3.16 (4H, m); 1.94–1.83 (4H, m); 1.8–1.86 (4H, m); 1.35 (3H, t).

C) Synthesis of 1-Ethyl-6-fluoro-1,4-dihydro-4-oxo-7-(1-pipera zinyl)-3-quinolinecarboxylic acid 4-nitrooxybutyl ester nitrate salt To a solution of 1-Ethyl-6-fluoro-1,4-dihydro-4-oxo-7-(1-piperazinyl)-3-quinolinecarboxylic acid 4-nitrooxybutyl ester (300 mg, 0.68 mmoles) in CH$_2$Cl$_2$ (5 ml) was added HCl—AcOEt 1 M (0.8 ml). After stirring for 1 hour at room temperature, the solvent was evaporated under a reduced pressure. The residue was dissolved in THF (10 ml) and silver nitrate (120 mg, 0.70 mmoles) was added. The mixture was stirred for 1 hour at room temperature, the suspension was filtered and the precipitate washed with THF and dried to afford 1-Ethyl-6-fluoro-1,4-dihydro-4-oxo-7-(1-piperazinyl)-3-quinolinecarboxylic acid 4-nitrooxybutyl ester nitrate salt (300 mg) as an amorphous solid. Yield 85%.

Elementary Analysis:

|  | % C | % H | % N | % F |
|---|---|---|---|---|
| calculated: | 48.10 | 5.25 | 14.02 | 3.80 |
| found: | 48.05 | 5.30 | 14.11 | 3.75 |

Example 18
Synthesis of 3-[[4-[1-Cyclopropyl-6-fluoro-1,4-dihydro-4-oxo-7-(1-piperazinyl)-3-quinolinecarbonyloxy]-3-methoxy]phenyl]-2-propenoic acid 4-(nitrooxybutyl)butyl ester nitrate salt

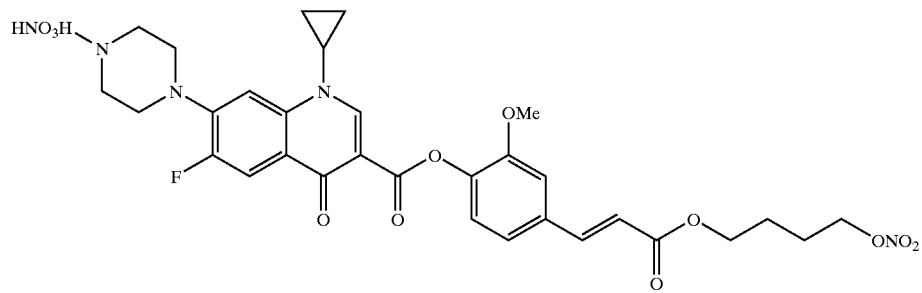

A) Synthesis of 1-Cyclopropyl-6-fluoro-1,4-dihydro-4-oxo-7-(N-tert-butoxycarbonyl-1-piperazinyl-)-3-quinolinecarboxylic acid To a suspension of 1-cyclopropyl-6-fluoro-1,4-dihydro-4-oxo-7-(1-piperazinyl-)-3-quinolinecarboxylic acid (3.31 g, 10 mmoles) in CH$_2$Cl$_2$ (120 ml) were added at room temperature TEA (4.21 ml, 30 mmoles) and di-tert-butyl dicarbonate (4.4 g, 30 mmoles). The mixture was stirred for 12 hours at room temperature. After cooling at –5° C. the suspension was filtered, the collected precipitate dissolved in CH$_2$Cl$_2$ (200 ml) and the resulting solution washed with aq AcOH 0.3 M (100 ml)

The organic phase was dried with sodium sulphate and the solvent was evaporated in vacuo. The residue was crystallized from a mixture CH$_2$Cl$_2$ (10 ml)/n-hexane (100 ml) to afford 1-Cyclopropyl-6-fluoro-1,4-dihydro-4-oxo-7-(N-tert-butoxy carbonyl-1-piperazinyl-)-3-quinolinecarboxylic acid (3.93 g). Yield 91% m.p. 248–249° C. (dec.)

B) Synthesis of 3-[[4-[1-Cyclopropyl-6-fluoro-1,4-dihydro-4-oxo-7-(N-tert-butoxycarbonyl-1-piperazinyl)-3-quinolinecarbonyloxy]-3-methoxy]phenyl]-2-propenoic acid 4-(nitrooxybutyl)butyl ester To a solution of 1-cyclopropyl-6-fluoro-1,4-dihydro-4-oxo-7-(N-tert-butoxycarbonyl-1-piperazinyl-)-3-quinolinecarboxylic acid (5.36 g, 12.43 mmoles) and of 3-[(3-methoxy-4-hydroxy)phenyl]-2-propenoic acid 4-nitrooxybutyl ester (3.78 g, 12.43 mmoles) in CH$_2$Cl$_2$ (100 ml) Ph$_3$P (4.89 g, 18.64 mmoli) and DEAP (2.94 ml, 18.64 mmoli) were added in the order. The mixture was stirred for 2 hours at room temperature, then the solvent was evaporated under reduced pressure. The residue was purified by chromatography on silica gel eluting with CH$_2$Cl$_2$/acetone (v/v 30/1) to afford 3-[4-[1-Cyclopropyl-6-fluoro-1,4-dihydro-4-oxo-7-(N-tert-butoxycarbonyl-1-piperazinyl)-3-quinolinecarbonyloxy]-3-methoxy]2-propenoic acid 4-(nitrooxybutyl)butyl ester (3.5 g). Yield 40%.

C) Synthesis of 3-[4-[1-Cyclopropyl-6-fluoro-1,4-dihydro-4-oxo-7-(1-piperazinyl)-3-quinolinecarbonyloxy]-3-methoxy]2-propenoic acid 4-(nitrooxybutyl)butyl ester hydrochloride To a solution of 3-[4-[1-Cyclopropyl-6-fluoro-1,4-dihydro-4-oxo-7-(N-tert-butoxycarbonyl-1-piperazinyl)-3-quinoline carbonyloxy]-3-methoxy]2-propenoic acid 4-(nitrooxybutyl)butyl ester (3.5 g) in CH$_2$Cl$_2$ (50 ml) was added HCl—AcOEt 20% (5 ml). After stirring for 2 hours at room temperature, the solvent was evaporated under a reduced pressure and the residue was dissolved in acetone (40 ml). After cooling at 0° C. for 30 minutes, the suspension was filtered and the collected precipitate washed with diethyl ether to afford 3-[4-[1-Cyclopropyl-6-fluoro-1,4-dihydro-4-oxo-7-(1-piperazinyl)-3-quinolinecarbonyloxy]-3-methoxy]2-propenoic acid 4-(nitrooxy butyl) butyl ester hydrochloride (2 g) as a yellow solid. m.p. 207–209° C.

$^1$H NMR (DMSO) ppm: 9.26 (1H, S), 8.68 (1H, S), 7.85 (1H, d), 7.68 (1H, d), 7.53 (2H, dd), 7.35 (1H, dd), 7.20 (1H, d), 6.74 (1H, d), 4.6 (2H, t), 4.2 (2H, t), 3.83 (3H, S), 3.76 (1H, m), 5.52 (4H, m), 3.33 (4H, s), 1.78 (4H, m), 1-32-1.16 (4H, m).

D) Synthesis of 3-[[4-[1-Cyclopropyl-6-fluoro-1,4-dihydro-4-oxo-7-(1-piperazinyl)-3-guinolinecarbonyloxy]-3-methoxy]phenyl]-2-propenoic acid 4-(nitrooxybutyl)butyl ester nitrate salt To a solution of 3-[[4-[1-Cyclopropyl-6-fluoro-1,4-dihydro-4-oxo-7-(1-piperazinyl)-3-quinolinecarbonyloxy]-3-methoxy]phenyl]-2-propenoic acid 4-(nitrooxybutyl)butyl ester hydro chloride (2 g, 3.03 mmoles) in THF (20 ml) was added silver nitrate (514 mg, 3.03 mmoles). After stirring for 1 hours at room temperature, the mixture was filtered and the precipitate washed with THF and dried to afford 3-[4-[1-Cycylopropyl-6-fluoro-1,4-dihydro-4-oxo-7-(1- piperazinyl)-3-quinolinecarbonyl oxy]-3-methoxy]2-propenoic acid 4-(nitrooxybutyl)butyl ester nitrate salt (2 g) as an amorphous solid. Yield 96%.

| | Elementary Analysis: | | | |
|---|---|---|---|---|
| | % C | % H | % N | % F |
| Calculated: | 54.78 | 5.17 | 9.98 | 2.71 |
| Found: | 54.69 | 5.15 | 9.99 | 2.69 |

Example 19
Synthesis of 4-(nitrooxy)butanoic Acid 2-methyl-5-nitro imidazole-1-ethyl ester nitrate salt

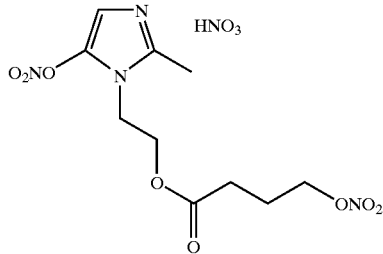

A) Synthesis of 4-bromobutanoic acid 2-methyl-5-nitro imidazole-1-ethyl ester

To a solution of metronidazole (7.5 g, 48.82 mmoles) in $CHCl_3$ (75 ml) and DMF (93 ml) 4-bromobutyrric acid (6.1 g, 36.51 mmoli) was added. After stirring the mixture for 24 hours at room temperature, the organic phase was washed with water, dried with sodium sulphate and evaporated under a reduced pressure.

The residue was purified by chromatography on a silica gel column eluted with metilene chlorid/acetone (v/v 9/1) to afford 4-Bromobutanoic acid 2-methyl-5-nitroimidazole-1-ethyl ester (6.5 g, 20.3 mmoles). Yield 55%.

B) Synthesis of 4-(nitrooxy)butanoic acid 2-methyl-5-nitro imidazole-1-ethyl Ester To a solution of 4-bromobutanoic acid 2-methyl-5-nitro imidazole-1-ethyl ester (6.4 g, 20.05 mmoles) in anhydrous acetonitrile (170 ml) silver nitrate (5.11 g, 30.07 mmoles) was added The mixture was heated at 40° C. for 48 hours in the darkness. The mixture was filtered and the filtrate was washed with water, dried with sodium sulphate and evaporated in vacuo.

The residue was purified by chromatography on a silica gel column by eluting with metilene chloride/acetone (v/v 9/1) to afford 4-(nitrooxy)butanoic acid 2-methyl-5-nitroimidazole-1-ethyl ester (3.68 g, 12.17 mmoli) as an oil. Yield 60%.

$^1$H NMR (DMSO) ppm: 8.08 (1H, s); 4.55 (2H, t); 4.53 (2H, t) 4.43 (2H, t); 2.51 (2R, s); 2.40 (2H, t); 1.91 (2H, m).

C) Synthesis of 4-(nitrooxy)butanoic acid 2-methyl-5-nitro imidazole-1-ethyl ester nitrate salt To a solution of 4-(nitrooxy)butanoic acid 2-methyl-5-nitroimidazole-1-ethyl ester (3.68 g, 12.17 mmoles) in $CH_2Cl_2$ (80 ml) was added HCl—AcOEt 1M (12.2 ml). After stirring for 1 hour at room temperature, the solvent was evaporated under a reduced pressure and the residue was dissolved in THF (75 ml). Silver nitrate (2 g, 12.17 mmoles) was added. The mixture was stirred for 1 hour at room temperature, the suspension filtered and the precipitate washed with THF and dried to afford 4-(nitrooxy)butanoic acid 2-methyl-5-nitroimidazole-1-ethyl ester nitrate salt (4.2 g) solid. Yield 90%.

| | Elementary Analisys: | | |
|---|---|---|---|
| | % C | % H | % N |
| Calculated: | 31.50 | 3.96 | 18.37 |
| Found: | 31.45 | 3.90 | 18.29 |

Example 20
Synthesis of 4-(nitrooxy)butanoic Acid 5-nitro-8-quinolinol ester nitrate salt

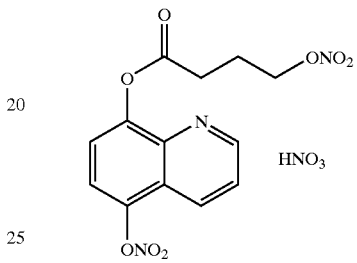

A) Synthesis of 4-bromobutanoic acid 5-nitro-8-quinolinol ester

To a solution of nitroxoline (4.32 g, 22.72 mmoles) and triethylamine (2.75 g, 27.26 mmol) in $CHCl_3$ (100 ml) and DMF (69 ml) 4-bromobutyrrilchloride (5.05 g, 27.26 mmoles) was added at 0° C. After stirring at room temperature for 24 hours, another portions of triethylamine (0.46 g, 4.5 mmol) and 4-bromobutyrril chloride (0.83 g, 4.5 mmoles) were added. The mixture was stirred for 48 hours at room temperature. Water and metilene chloride were added and, after separation of the two phases the organic layer was washed with water, dried with sodium sulphate and evaporated under a reduced pressure.

The residue was purified by chromatography on silica gel column eluted with ethyl acetate/n-hexane (v/v 2/8) to afford 4-bromobutanoic acid 5-nitro-8-quinolinol ester (6.86 g, 20.22 mmoles) as an oil. Yield 90%.

$^1$H NMR ($CDCl_3$) ppm: 9.06 (2H, m); 8.44 (1H, d); 7.65 (1H, m); 7.5 (1H, d); 3.66 (2H, m); 3.03 (2H, m); 2.42 (2H, m).

B) Synthesis of 4-(nitrooxy)butanoic acid 5-nitro-8-quinolinol ester

To a solution of 4-bromobutanoic acid 5-nitro-8-quinolinol ester (6.86 g, 20.2 mmoles) in anhydrous acetonitrile (100 ml) silver nitrate (13.65 g, 80.3 mmoles) was added. The mixture was heated at 40° C. for 64 hours in the darkness. The mixture was then filtered, the filtrate dried with sodium sulphate and evaporated under reduced pressure. The residue was purified by chromatography on a silica gel column eluted with ethyl acetate/n-hexane (v/v 3/7) to afford 4-(nitrooxy)butanoic acid 5-nitro-8-quinolinol ester (2.05 g, 6.38 mmoles) as an yellow amorphous solid. Yield 31%. (m.p.=68° C.).

$^1$H NMR (DMSO) ppm: 9.02 (1H, dd); 8.97 (1H, d); 8.45 (1H, dd); 7.65 (1H, m); 7.54 (1H, dd); 4.74 (2H, t); 2.97 (2H, t); 2.03 (2H, m).

C) Synthesis of 4-(nitrooxy)butanoic acid 5-nitro-8-quinolinol ester nitrate salt To a solution of 4-(nitrooxy)butanoic acid 5-nitro-8-quinolinol ester (2.05 g, 6.38 mmoles) in ethyl acetate (40 ml) was added HCl—AcOEt 1M (6.4 ml). After stirring for 1 hour at room temperature, the solvent was evaporated under a reduced pressure and the residue was dissolved in THF (50 ml) and added of silver nitrate (1.08 g, 6.38 mmoles). The mixture was stirred for 1 hour at room temperature, the suspension was filtered and the precipitate was washed with THF, dried to afford 4-(nitrooxy)butanoic acid 2-methyl-5-nitroimidazole-1-ethyl ester nitrate salt (2.2 g) solid. Yield 89%.

Elementary Analisys:

|  | % C | % H | % N |
|---|---|---|---|
| Calculated: | 39.01 | 3.22 | 13.99 |
| Found: | 38.94 | 3.14 | 13.91 |

Example 21

Synthesis of 6-(D-(−)-alfa-aminophenylacetamido) pennicillanic acid 4-(nitrooxy)butyl ester nitrate salt

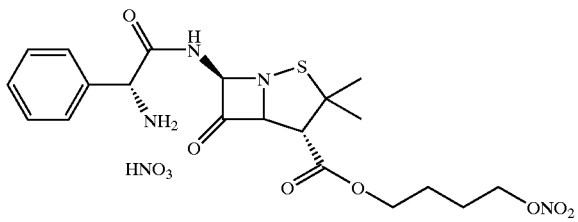

A) Synthesis of 6-(D-(−)-alfa-aminophenylacetamido) pennicillanic sodium salt

To a solution of ampicillin (5.09 g, 14.6 mmoles) in absolute ethanol (120 ml) sodium ethylate (0.99 g, 14.6 mmoles) was added. The mixture was stirred for 1 hour at room temperature and then for at 60° C. 30 minutes. The mixture was evaporated under a reduced pressure to afford 6-(D-(−)-alfa-aminophenylacetamido)pennicillanic sodium salt (5.4 g, 14.5 mmoles) as a white solid. Yield 99%.

B) Synthesis of 6-(D-(−)-alfa-tert-butoxycarbonylaminophenyl acetamido) pennicillanic acid To a solution of 6-(D-(−)-alfa-aminophenylacetamido) pennicillanic sodium salt (5.4 g, 14.57 mmoles) in 1,4-dioxane (166 ml) and water (121 ml), at a temperature of 0° C. a solution of di-tert-butyl dicarbonate (5.08 g, 23.31 mmoles) in 1,4-dioxane (45 ml) was added. When the addition was ended, the temperature was raised at room temperature and stirring was continued for 48 hours. The mixture was then evaporated under a reduced pressure. The residue was dissolved in aqueous NaHCO$_3$ 5%, washed with diethyl ether; the pH value of the aqueous phase was adjusted to the value of 2 by adding at a temperature of 0° C. H$_3$PO$_4$ 50% (11 ml). After extraction of the aqueous phase with ethyl acetate, the combined organic phases were dried and evaporated under a reduced pressure to afford 6-(D-(−)-α-tert-butoxycarbonylaminophenylacetamido) pennicillanic acid, that was used without further purification.

$^1$H NMR (CDCl$_3$) ppm: 7.34 (5H, s); 6.85 (1H, bs); 5.8 (1H, bs); 5.6 (1H, dd); 5.45 (1H, d); 5.22 (1H, bs); 4.38 (1H, s); 1.4 (15H, m).

B) Synthesis of 6-(D-(−)-alfa-aminophenylacetamido) pennicillanic acid 4-bromobutyl ester To a solution of 6-(D-(−)-alfa-tert-butoxycarbonyl aminophenylacetamido)pennicillanic acid (6.36 g, 14.15 mmoles) in DMF (60 ml) triethylamine (2.76 ml, 19.81 mmoles) was added. After stirring for 30 minutes, 1,4-dibromobutane (6.11 g, 28.30 mmoles) was added and the mixture stirred for 12 hours.

Diethyl ether was then added at the suspension and Et$_3$N.HBr was filtered off. The organic phase was washed with water, dried with sodium sulphate and evaporated under a reduced pressure.

The residue was purified by chromatography on silica gel column eluted with ethyl acetate/n-hexane (v/v 15/85) to afford 6-(D-(−)-alfa-aminophenylacetamido)pennicillanic acid 4-bromo butyl ester (3.2 g) as a white solid.

$^1$H NMR (CDCl$_3$) ppm: 7.35 (5H, m); 6.6 (1H, bs); 5.6 (1H, m); 5.4 (1H, d); 5.2 (1H, bs); 4.39 (1H, s), 4.18 (2H, m); 3.42 (2H, t); 1.9 (4H, m); 1.4 (15H, m).

C) 6-(D-(−)-alfa-aminophenylacetamido)pennicillanic acid 4-nitrooxy butyl ester

To a solution of 6-(D-(−)-alfa-aminophenylacetamido) pennicillanic acid 4-bromobutyl ester (3.12 g, 5.34 mmoles) in acetonitrile (50 ml) silver nitrate (1.27 g, 7.48 mmoles) was added. The mixture was heated at 40° C. for 10 hours in the darkness. Then mixture was filtered and evaporated under a reduced pressure. The residue was purified by chromatography on a silica gel column by eluting with ethyl acetate/n-hexane v/v 3/7) to afford 6-(D-(−)-alfa-aminophenylacetamido) pennicillanic acid 4-nitrooxybutyl ester (0.9 g) as a yellow amorphous solid.

$^1$H NMR (CDCl$_3$) ppm: 7.35 (5H, m); 6.6 (1H, bs); 5.6 (1H, m); 5.4 (1H, m); 5.2 (1H, bs); 4.5 (2H, m); 4.4 (1H, s); 4.2 (2H, m); 1.8 (4H, bs); 1.4 (15H, m).

D) 6-(D-(−)-alfa-aminophenylacetamido)pennicillanic Acid 4-nitro Oxy Butyl Ester Nitrate Salt To a solution of 6-(D-(−)-alfa-aminophenylacetamido) pennicillanic acid 4-nitrooxybutyl ester (0.9 g, 1.58 mmoles) in ethyl acetate (10 ml) a solution HCl 1M in AcOEt (1.5 ml) was added at 0° C. The mixture was stirred at 0° C. for 20 minutes and for 1 hour at room temperature. The solvent was evaporated under a reduced pressure, the residue dissolved in THF (5 ml) and the solution added of silver nitrate (268 mg, 1.58 mmoles). The mixture was stirred for 1 hour at room temperature, then filtered, and the precipitate washed with THF and dried to afford 6-(D-(−)-alfa-aminophenylacetamido)pennicillanic acid 4-nitrooxybutyl ester nitrate salt (736 mg) solid. Yield 88%.

Elementary Analisys:

|  | % C | % H | % N | % S |
|---|---|---|---|---|
| Calculated: | 45.36 | 5.14 | 13.22 | 6.05 |
| Found: | 45.28 | 5.08 | 13.16 | 5.97 |

TABLE 1

Strain *E. Coli* (ATCC25922): Antimicrobial activity of Cefazolin and Cefazolin nitrate salt, Ampicillin and Ampicillin nitrate salt.

| COMPOUND | CONCENTRATION (µg/ml) | RESPONSE |
|---|---|---|
| Cefazolin | 0.5 | Growth |
| Cefazolin.HNO$_3$ | 0.5 | No growth |
| Ampicillin | 1.0 | Growth |
| Ampicillin.HNO$_3$ | 1.0 | No growth |

TABLE 2

Strain *S. Aureus* (ATCC29213) Antimicrobial activity of Clindamycin and Clindamycin nitrate salt, Ciprofloxacin and Ciprofloxacin nitrate salt, Sulfamethoxazole and Sulfamethoxazole nitrate salt, Trimethoprim and Trimethoprim nitrate salt, Erythromycin and Erythromycin nitrate salt.

| COMPOUND | CONCENTRATION (µg/ml) | RESPONSE |
|---|---|---|
| Clindamycin | 0.03 | Growth |
| Clindamycin.HNO$_3$ | 0.03 | No growth |
| Ciprofloxacin | 0.05 | Growth |
| Ciprofloxacin.HNO$_3$ | 1.0 | No growth |
| Sulfamethoxazole | 20 | Growth |
| Sulfamethoxazole.HNO$_3$ | 20 | No growth |
| Trimethoprim | 0.5 | Growth |
| Trimethoprim.HNO$_3$ | 0.5 | No growth |
| Erythromycin | 0.06 | Growth |
| Erythromycin.HNO$_3$ | 0.06 | No growth |

What is claimed is:

1. A nitrate salt of an antimicrobial compound having formula II:

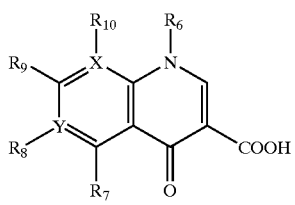

(II)

wherein:

X and Y, different from one another, are C or N, $R_6$=cyclopropyl, $C_2H_5$, 4-fluorophenyl, 2,4-difluorophenyl, or 2-fluoroethyl, $R_7$=H; amino, or $CH_3$, $R_8$=H or F, or when Y=N, $R_8$ is the free electron doublet on the nitrogen atom, which forms a double bond with the carbon atom adjacent the nitrogen, $R_9$=H or $CH_3$ or one of the following substituents:

(IIA)

wherein M=H, $CH_3$, $C_2H_5$, OH,

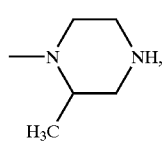

(IIB)

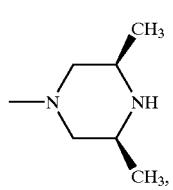

(IIC)

(IID)

(IIE)

wherein $T_1$ is H, OH

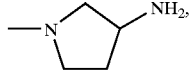

(IIF)

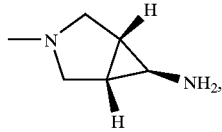

(IIG)

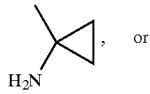

(IIH)

, or $R_8$ and $R_9$ taken together form the bivalent radical having formula:

—O—CH$_2$—O—  (IIP), $R_{10}$=H, Cl, F, or when X=N, $R_{10}$ is the free electron doublet on the nitrogen atom, which forms a double bond with the carbon atom adjacent the nitrogen, or $R_8$ and $R_{10}$ taken together form the following bivalent radicals:

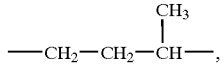

(IIM)

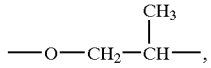

(IIN)

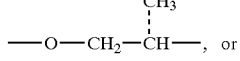

(IIO)

—S—CH$_2$—CH$_2$—.  (IIQ)

2. The nitrate salt according to claim 1, selected from the following:

when $R_6$=cyclopropyl, $R_7$=H, $R_8$=F, $R_9$=(IIA) with M=H, $R_{10}$=H, X=Y=C, the compound is known as Ciprofloxacin, when $R_6$=cyclopropyl, $R_7$=H, $R_8$=F, $R_9$=(IIF), $R_{10}$=Cl, X=Y=C, the compound is known as Clinaloxacin, when $R_6$=4-fluorophenyl, $R_7$=H, $R_8$=F, $R_9$=(IID), $R_{10}$=H, X=Y=C, the compound is known as Difloxacin, when $R_6$=$C_2H_5$, $R_7$=H, $R_8$=F, $R_9$=(IIA) with M=H, $R_{10}$= free valence, X=N, Y=C, the compound is known as Enoxacin, when $R_6$=cyclopropyl, $R_7$=H, $R_8$=F, $R_9$=(IIA) with M=$C_2H_5$, $R_{10}$=H, X=Y=C, the compound is known as Enrofloxacin, when $R_6$=fluoroethyl, $R_7$=H, $R_8$=F, $R_9$=(IIA) with M=CH$_3$, $R_{10}$=F, X=Y=C, the compound is known as Fleroxacin, when $R_6$ with $R_{10}$ forms the bivalent radical (IIM), $R_7$=H, $R_8$=F, $R_9$=H, X=Y=C, the compound is known as Flumequine, when $R_6$=cyclopropyl, $R_7$=CH$_3$, $R_8$=F, $R_9$=(IIB), $R_{10}$=H, X=Y=C, the compound is known as Gre-pafloxacin, when $R_6$=ethyl, $R_7$=H, $R_8$=F, $R_9$=(IIB), $R_{10}$=F, X=Y=C, the compound is known as Lomefloxacin, when $R_6$ with $R_{10}$ forms the bivalent radical (IIM), $R_7$=H, $R_8$=F, $R_9$=(IIE) with $T_1$=OH, X=Y=C, the compound is known as Nadifloxacin, when $R_6$=C$_2$H$_5$, $R_7$=H, $R_8$=H, $R_8$=CH$_3$, $R_{10}$=free valence, X=N, Y=C, the compound is known as Na-lidixic Acid, when $R_6$=C$_2$H$_5$, $R_7$=H, $R_8$=F, $R_9$=(IIA) with M=H, $R_{10}$=H, X=Y=C, the compound is known as Norfloxacin, when $R_6$ with $R_{10}$ forms the bivalent radical (IIN), $R_7$=H, $R_8$=F, $R_9$=(IIA) with M=CH$_3$, X=Y=C, the compound is known as Ofloxacin, when $R_6$=C$_2$H$_5$, $R_7$=H, $R_8$ and $R_9$ form the bivalent radical (IIP), $R_{10}$=H, X=Y=C, the compound is known as Oxolinic Acid, when $R_6$ with $R_{10}$ forms the bivalent radical (IIO), $R_7$=H, $R_8$=F, $R_9$=(IIH), X=Y=C, the compound is known as Pazufloxacin, when $R_6$=ethyl, $R_7$=H, $R_8$=F, $R_9$=(IIA) with M=CH$_3$, $R_{10}$=H, X=Y=C, the compound is known as Pefloxacin, when $R_6$=C$_2$H$_5$, $R_7$=H, $R_8$=free valence, $R_9$=(IIA) with M=H, $R_{10}$=free valence, X=Y=N, the compound is known as Pipemidic Acid, when $R_6$=C$_2$H$_5$, $R_7$=H, $R_8$=free valence, $R_9$=(IIE) with $T_1$=H, $R_{10}$=free valence, X=Y=N, the compound is known as Piromidic Acid, when $R_6$ with $R_{10}$ forms the bivalent radical (IIQ), $R_7$=H, $R_8$=F, $R_9$=(IIA) with M=CH$^3$, X=Y=C, the compound is known as Rufloxacin, when $R_6$=cyclopropyl, $R_7$=amino, $R_8$=F, $R_9$=(IIC), $R_{10}$=F, X=Y=C, the compound is known as Sparfloxacin, when $R_6$=2,4-difluorophenyl, $R_7$=H, $R_8$=F, $R_9$=(IIE), $R_{10}$=free valence, X=N, Y=C, the compound is known as Tosufloxacin, when $R_6$=2,4-difluorophenyl, $R_7$=H, $R_8$=F, $R_9$=(IIG), $R_{10}$=free valence, X=N, Y=C, the compound is known as Trovafloxacin, when $R_6$=cyclopropyl, $R_7$=H, $R_8$=F, $R_9$=(IID), $R_{10}$=H, X=Y=C, the compound is known as Danofloxacin, or when $R_6$=4-fluorophenyl, $R_7$=H, $R_8$=F, $R_9$=(IIA) with M=H, $R_{10}$=H, X=Y=C, the compound is known as Sarafloxacin.

3. The nitrate salt according to claim 2 selected from the following:

when $R_6$=cyclopropyl, $R_7$=H, $R_8$=F, $R_9$=(IIA) with M=H, $R_{10}$=H, X=Y=C, the compound is known as Ciprofloxacin, when $R_6$=C$_2$H$_5$, $R_7$=H, $R_8$=H, $R_9$=CH$_3$, $R_{10}$=free valence, X=N, Y=C, the compound is known as Nalidixic acid, when $R_6$=C$_2$H$_5$, $R_7$=H, $R_8$=F, $R_9$=(IIA) with M=H, $R_{10}$=H, X=Y=C, the compound is known as Norfloxacin, or when $R_6$ with $R_{10}$ forms the bivalent radical (IIN), $R_7$=H, $R_8$=F, $R_9$=(IIA) with M=CH$_3$, X=Y=C, the compound is known as Ofloxacin.

4. The nitrate salt according to claim 1 wherein in their molecules there are one or more substituents having the formula (I-N)

$$-B-(W)_p-ONO_2 \qquad \text{(I-N)}$$

wherein:

p is 1 or 0;

B=—$T_B$—Y—$T_{BI}$— wherein $T_B$ and $T_{BI}$ are same or different;

$T_B$ is a chemical function covalently linked to the chemical or reacting function of the drug molecule and is (CO) or X, wherein X=O, S, NH, with the condition that X=(CO) when the reacting function of the drug is OH or NH$_2$ or SH; $T_B$ is X when the reacting function of the drug is a carboxyl group;

$T_{BI}$=(CO)$_{tx}$ or (X)$_{txx}$, wherein tx and txx are 0 or 1; with the condition that tx=1 when txx=0, tx=0 when txx=1; X is as above defined;

Y is a bivalent linking bridge chosen between the following structures:

$$\begin{array}{c} R_{TIX} \quad\quad R_{TIIX} \\ | \quad\quad\quad | \\ -[C]_{nIX}-Y^3-[C]_{nIIX}- \\ | \quad\quad\quad | \\ R_{TIX'} \quad\quad R_{TIIX'} \end{array} \qquad \text{(II-Y)}$$

wherein:

nIX is an integer selected from 0, 1, 2, or 3;

nIIX is an integer selected from 0, 1, 2, or 3;

$R_{TIX}$, $R_{TIX'}$, $R_{TIIX}$, $R_{TIIX'}$, same or different each from the other, are H or linear or branched $C_1$–$C_4$ alkyl;

$Y^3$ is a ring containing at least one salifiable nitrogen atom;

an alkylene group R' wherein R' is a linear or branched $C_1$–$C_{20}$ alkyl, optionally substituted with one or more of the following groups: —NHCOR$_{3Y}$, wherein $R_{3Y}$ is a linear or branched $C_1$–$C_5$ alkyl, —NH$_2$, or —OH, a cycloalkylene ring $C_5$–$C_7$, optionally substituted with R', being R' as above defined, wherein one or more C atoms of the cycloalkylene can be optionally substituted with heteroatoms;

$$\text{(III-Y)}$$

(structure showing benzene ring with —(CH$_2$)$_{n3}$— and —(CH$_2$)$_{n3'}$— substituents)

wherein n3 is an integer from 0 to 3 and n3' is an integer from 1 to 3;

(structure showing ring with (CH$_2$)$_{n3'}$, HOOC and (CH$_2$)$_{n3}$ substituents)

wherein n3 and n3' have the meanings above indicated;

(V-Y)

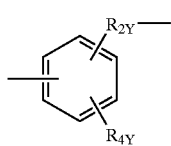

wherein:
$R_{4Y}$ is OH, or H, alcoxy $R_{5Y}O$— wherein $R_{5Y}$ is a linear or branched or cyclo $C_1$–$C_{10}$ alkyl;
$R_{2Y}$ is a linear or branched alkenylene $C_2$–$C_{10}$ containing one or more double bonds;

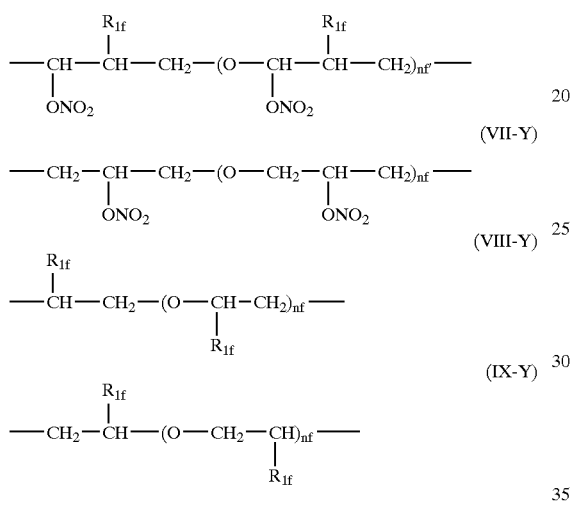

wherein $R_{1f}$=H, $CH_3$ and nf is an integer from 0 to 6;

W of formula (I-N) is the bivalent radical —$T_C$—$Y_T$- wherein:
$T_c$=(CO) when $t_x$=0, $T_c$=X when $t_{xx}$=0;
with the proviso that in formula (I-N) when p=1 $Y_T$ is different from Y and in the bivalent radical B:
Y is R' as above defined having a substituent $NHCOR_{3Y}$, or
Y is a bivalent radical of formula (V-Y), wherein $R_{4Y}$ is $OR_{5Y}$ and $R_{5Y}$ is $CH_3$, $R_{2Y}$ is the group —CH=CH—.

5. The nitrate salt according to claim 4 wherein $Y^3$ in formula (II-Y) is selected from the following bivalent radicals:

(Y1)
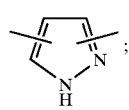

(Y2)
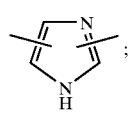

(Y3)
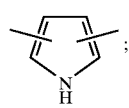

(Y4)

(Y5)

(Y6)

(Y7)
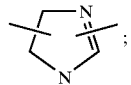

(Y8)
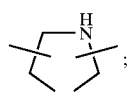

(Y9)
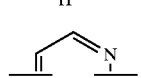

(Y10)
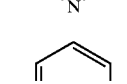

(Y11)
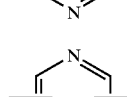

(Y12)
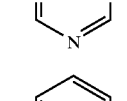

(Y13)
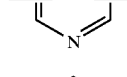

(Y14)
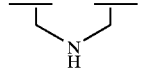

(Y15)
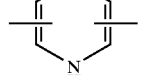

6. The nitrate salt according to claim 5 wherein $Y^3$ is a 6-membered aromatic ring containing one nitrogen atom, said ring having the two free valences in the following positions: 2,6; 2,3; or 2,5.

7. The nitrate salt according to claim 6 wherein $Y^3$ is Y12 substituted at positions 2 and 6.

8. A composition comprising the nitrate salt according to claim 1 wherein one or more isomers of the compounds are included.

9. The nitrate salt according to claim 1 containing one nitrate ion mole/compound mole.

10. The nitrate salt according to claim 1 containing one substituent of the formula (I-N).

11. The nitrate salt according to claim 4 wherein $R_{TIX}$, $R_{TIX'}$, $R_{TIIX}$, and $R_{TIIX'}$ are H.

12. The nitrate salt according to claim 4, wherein Y is a heterocyclic ring containing one or two nitrogen atoms, the ring saturated, unsaturated or aromatic.

13. The nitrate salt according to claim 4, wherein the ring has 5 or 6 atoms.

14. The nitrate salt according to claim 4, wherein R' is a $C_2$–$C_6$ alkyl and/or $R_{5Y}$ is methyl.

15. The nitrate salt according to claim 4, wherein $R_{2Y}$ is an ethylene group (—CH—CH).

16. The nitrate salt according to claim 4, wherein nf is an integer from 0 to 4.

17. The nitrate salt according to claim 4, wherein in formula (I-N) when p=1 $Y_T$ is different from Y and in the bivalent radical B:
R' is a $C_2$ saturated alkyl and $R_{3Y}$ is $CH_3$.

18. The nitrate salt according to claim 4, wherein in formula (I-N) when p=1 $Y_T$ is different from Y and in the bivalent radical B:
Y is $CH_2$—$CH(NHCOCH_3)$— and B in formula (I-N) has the following structure:

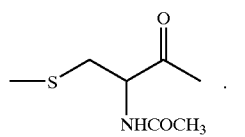

(X-Y)

19. The nitrate salt according to claim 4, wherein in formula (I-N) when p=1 $Y_T$ is different from Y and in the bivalent radical B:
Y has the following formula:

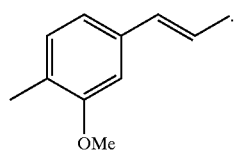

(XI-Y)

20. A pharmaceutical composition, comprising a compound having formula II:

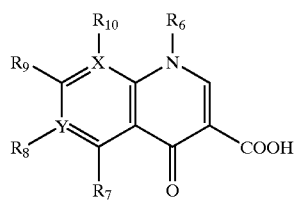

(II)

wherein:
X and Y, different from one another, are C or N,
$R_6$=cyclopropyl, $C_2H_5$, 4-fluorophenyl, 2,4-difluorophenyl, or 2-fluoroethyl, $R_7$=H, amino or $CH_3$, $R_8$=H or F, or when Y=N, $R_8$ is the free electron doublet on the nitrogen atom, which forms a double bond with the carbon atom adjacent the nitrogen, $R_9$=H, $CH_3$ or one of the following substituents:

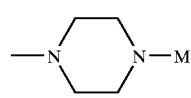

(IIA)

wherein M=H, $CH_3$, $C_2H_5$, or OH,

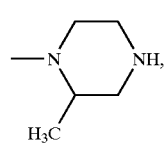

(IIB)

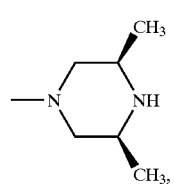

(IIC)

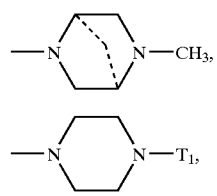

(IID)

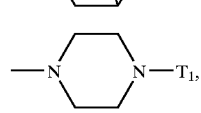

(IIE)

wherein $T_1$ is H, OH

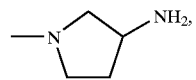

(IIF)

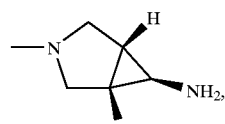

(IIG)

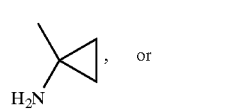

(IIH)

$R_8$ and $R_9$ taken together form the bivalent radical having formula: —O—$CH_2$—O— (IIP), $R_{10}$=H, Cl, or F, or when X=N, $R_{10}$ is the free electron doublet on the nitrogen atom, which forms a double bond with the carbon atom adjacent the nitrogen, or $R_6$ and $R_{10}$ taken together form the following bivalent radicals:

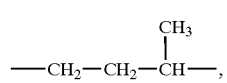

(IIM)

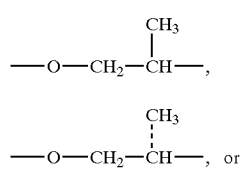
(IIN)
 (IIQ)
(IIO)
and a pharmaceutical carrier.
* * * * *